United States Patent
Zhou

(10) Patent No.: US 9,340,597 B2
(45) Date of Patent: *May 17, 2016

(54) NEUREGULIN VARIANTS AND METHODS OF SCREENING AND USING THEREOF

(71) Applicant: ZENSUN (SHANGHAI) SCIENCE AND TECHNOLOGY LTD., Shanghai (CN)

(72) Inventor: Mingdong Zhou, Shanghai (CN)

(73) Assignee: Zensun (Shanghai) Science And Technology Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,616

(22) Filed: Mar. 21, 2013

(65) Prior Publication Data

US 2014/0031284 A1   Jan. 30, 2014

Related U.S. Application Data

(60) Division of application No. 12/095,904, filed as application No. PCT/CN2006/003240 on Dec. 4, 2006, now Pat. No. 8,476,405, which is a continuation-in-part of application No. 11/293,879, filed on Dec. 2, 2005, now abandoned.

(51) Int. Cl.
| | |
|---|---|
| C07K 14/47 | (2006.01) |
| G01N 33/68 | (2006.01) |
| A61K 38/00 | (2006.01) |
| C07K 14/475 | (2006.01) |

(52) U.S. Cl.
CPC ........ C07K 14/4756 (2013.01); G01N 33/6872 (2013.01); *A61K 38/00* (2013.01); *G01N 2333/4756* (2013.01); *G01N 2500/02* (2013.01); *G01N 2800/32* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,179,337 A | 12/1979 | Davis et al. | |
| 4,301,144 A | 11/1981 | Iwashita et al. | |
| 4,485,045 A | 11/1984 | Regen | |
| 4,496,689 A | 1/1985 | Mitra | |
| 4,544,545 A | 10/1985 | Ryan et al. | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,367,060 A | 11/1994 | Vandlen et al. | |
| 5,530,109 A | 6/1996 | Goodearl et al. | |
| 5,586,110 A | 12/1996 | Nakaki et al. | |
| 5,641,869 A | 6/1997 | Vandlen et al. | |
| 5,667,780 A | 9/1997 | Ho et al. | |
| 5,714,385 A | 2/1998 | Mather et al. | |
| 5,716,930 A | 2/1998 | Goodearl et al. | |
| 5,721,139 A | 2/1998 | Mather et al. | |
| 5,834,229 A | 11/1998 | Vandlen et al. | |
| 5,840,525 A | 11/1998 | Vandlen et al. | |
| 5,859,206 A | 1/1999 | Vandlen et al. | |
| 5,968,511 A | 10/1999 | Akita et al. | |
| 6,033,660 A | 3/2000 | Mather et al. | |
| 6,087,323 A | 7/2000 | Gwynne et al. | |
| 6,096,873 A | 8/2000 | Schaefer et al. | |
| 6,121,415 A | 9/2000 | Godowski et al. | |
| 6,136,558 A | 10/2000 | Ballinger et al. | |
| 6,156,728 A | 12/2000 | Gao et al. | |
| 6,162,641 A | 12/2000 | Goldman et al. | |
| 6,169,070 B1 | 1/2001 | Chen et al. | |
| 6,252,051 B1 | 6/2001 | Godowski et al. | |
| 6,387,638 B1 | 5/2002 | Ballinger et al. | |
| 6,399,746 B1 | 6/2002 | Vandlen et al. | |
| 6,444,642 B1 | 9/2002 | Sklar et al. | |
| 6,446,242 B1 | 9/2002 | Lien et al. | |
| 6,593,290 B1 | 7/2003 | Gao et al. | |
| 6,635,249 B1 | 10/2003 | Marchionni et al. | |
| 6,750,196 B1 | 6/2004 | Reh et al. | |
| 7,226,907 B1 | 6/2007 | Zhou | |
| 2006/0019888 A1 | 1/2006 | Zhou | |
| 2006/0194734 A1 | 8/2006 | Zhou | |
| 2006/0199767 A1 | 9/2006 | Zhou | |
| 2007/0129296 A1 | 6/2007 | Zhou | |
| 2007/0213264 A1 | 9/2007 | Zhou | |
| 2007/0264254 A1 | 11/2007 | Zhou | |

FOREIGN PATENT DOCUMENTS

| | | |
|---|---|---|
| AU | 68278/94 A | 12/1994 |
| CN | 1138785 C | 2/2004 |
| CN | 1498656 A | 5/2004 |
| CN | 1715926 A | 1/2006 |
| DE | 3218121 A1 | 11/1983 |
| EP | 0036676 A1 | 9/1981 |
| EP | 0052322 A2 | 5/1982 |

(Continued)

OTHER PUBLICATIONS

Galindo et al., Curr Heart Fail Rep, 11(1):40-49, Mar. 2014.*
Balligand et al., "Cardiac endothelium and tissue growth," Prog CArdiovasc Dis., 39(4):351-360 (1997).
Chien et al., "Regulation of cardiac gene expression during myocardial growth and hypertrophy: molecular studies of an adaptive physiologic response," FASEB J., 5(15):3037-3046 (1991).
Colucci et al., "Pathphysiology of heart failure," Chapter 13 in Heart Diseases: A textbook of cardiovascular medicine, Braunwald, ed., Saunders, PA, 5:394-420 (1996).
Dias et al., "The molecular basis of skeletal muscle differentiation," Semin Diagn Pathol. 11(1):3-14 (1994).

(Continued)

*Primary Examiner* — Daniel E Kolker
*Assistant Examiner* — Stacey N MacFarlane
(74) *Attorney, Agent, or Firm* — Jones Day

(57) ABSTRACT

The present invention provides polypeptide variants of neuregulin-1β (NRG-1β) that have enhanced or decreased binding affinity to ErbB3 and/or ErbB4. The invention also provides methods of screening and producing polypeptide variants of NRG-1β and methods of using polypeptide variants of NRG-1β for treating diseases.

15 Claims, 17 Drawing Sheets

(56) References Cited

FOREIGN PATENT DOCUMENTS

| | | |
|---|---|---|
| EP | 0058481 A1 | 8/1982 |
| EP | 0088046 A2 | 9/1983 |
| EP | 0102324 A2 | 3/1984 |
| EP | 0143949 A1 | 6/1985 |
| EP | 0133988 A2 | 3/1995 |
| EP | 0647449 A1 | 4/1995 |
| EP | 0142641 A2 | 5/1995 |
| JP | 60007934 A | 1/1985 |
| WO | 89/01489 | 2/1989 |
| WO | 92/18627 | 10/1992 |
| WO | 94/00140 | 1/1994 |
| WO | 94/26298 | 11/1994 |
| WO | 95/32724 | 12/1995 |
| WO | 96/15812 | 5/1996 |
| WO | 97/09425 | 3/1997 |
| WO | 99/18976 | 4/1999 |
| WO | 00/37095 | 6/2000 |
| WO | 01/64877 | 9/2001 |
| WO | 03/099300 | 12/2003 |
| WO | 03/099320 | 12/2003 |
| WO | 03/099321 | 12/2003 |

OTHER PUBLICATIONS

Eppstein et al., "Biological activity of liposome-encapsulated murine interferon gamma is mediated by a cell membrane receptor," Proc. Natl. Acad. Sci., USA, 82(11):3688-3692 (1985).

Florini et al., "Stimulation of myogenic differentiation by a neuregulin, glial growth factor 2," J. Biol. Chem., 271 (22):12699-12702 (1996).

Holmes et al., "Identification of heregulin, a specific activator of p185erbB2," Science, 256(5060):1205-1210 (1992).

Hwang et al., "Hepatic uptake and degradation of unilamellar sphinogmyelin/cholesterol liposomes: a kinetic study," Proc. Natl. Acad. Sci., USA, 77(7):4030-4034 (1980).

Jones et al., "Binding interaction of the heregulinbeta egf domain with ErbB3 and ErbB4 receptors assessed by alanine scanning mutagenesis," J. Biol. Chem., 273(19):11667-11674 (1998).

Langer et al., "Biocompatibility of polymeric delivery systems for macromolecules," J. Biomed. Mater Res. 15 (2):267-277 (1981).

Luo et al., "Computational analysis of molecular basis of 1:1 interactions of NRG-1beta wild-type and variants with ErbB3 and ErbB4," Proteins, 59(4):742-756 (2005).

MeSH entry for Neuregulin-1, retrieved online from http:www.ncbi.nlm.nih.gov/mesh/68020890, entry dated 2000. Retrieved on Sep. 19, 2011.

Parker et al., "p53-independent expression of p21Cip1 in muscle and other terminally differentiating cells," Science, 267(5200):1024-1027 (1995).

Physicians' Desk Reference, Medical Economics Data Production Co., Montvale, NJ, pp. 2314-2320 (1994).

Rumyantsev, "Interrrelations of the proliferation and differeniation processes during cardiac myogenesis and regeneration," Int. Rev. Cytol., 51:186-273 (1977).

Sidman et al., "Controlled release of macromolecules and pharmaceuticals from synthetic polypeptides based on glutamic acid," Biopolymers, 22(1):547-556 (1983).

Simpson et al., "Myocyte hypertrophy in neonatal rat heart cultures and its regulation by serum and by catecholamines," Circ. Res. 51(6):787-801 (1982).

Zhao et al., "Neuregulins promote survival and growth of cardiac myocytes. Persistence of ErbB2 and ErbB4 expression in neonatnal and adult ventricular myocytes," J. Biol. Chem., 273(17):10261-10269 (1998).

Zhao et al., "Selective disruption of neuregulin-1 function in vertebrate embryos using ribozyme-tRNA transgenes," Development, 125(10):1899-1907 (1998).

Zhao et al., "Retinoid-dependent pathways suppress myocardial cell hypertrophy," Proc. Natl., Acad. Sci., USA, 92 (16):7391-7395 (1995).

Gray H., Gray's Anatomy: The Anatomical Basis of Medicine and Surgery, Williams et al., Ed., Churchill Livingstone, Edinburgh, pp. 264-265, 298-310 and 739-771 (1995).

International Search Report dated Apr. 12, 2007, for PCT/CN2006/003694.

International Search Report dated Mar. 10, 2000, for International Application No. PCT/AU99/01137.

Britsch et al., "The ErbB2 and ErbB3 receptors and their ligand, neuregulin-1, are essential for development of the sympathetic nervous system," Genes Dev., 12:1825-1836 (1998).

Massova and Kollman, "Computational alanine scanning to probe protein-protein interactions: a novel approach to evaluate binding free energies," J. Am. Chem. Soc., 121(36):8133-8143 (1999).

* cited by examiner

Fig.1A

```
EGFR    LEEKCQGTSNKLTQLGTFEDHFLSLQRMFNNCEVVLGNLEITYVQRNYDLSFLKTIQEVA
ErbB3   --AVCPGTLNGLSVTGDAENQYQTLYKLYERCEVVMGNLEIVLTGHNADLSPLQWVREVT
        ** ** * *:  *  *:::  :* ::::.****:*****. . :* *****: ::**:

EGFR    GYVLIALNTVERIPLENLQIIRGNMYYENSYALAVLSNYDANKT-GLKELPMRNLQEILH
ErbB3   GYVLVAMNEFSTLPLPNLRVVRGTQVYDGKFAIFVMLNYNTNSSHALRQLRLTQLTEILS
        ****:*:*  .. :** **::::**.  *:..:*: *: **::*.:  .*:*  : :* ***

EGFR    GAVRFSNNPALCNVESIQWRDIVSSDFLSNMSMDFQNHLGSCQKCDPSCPNGSCWGAGEE
ErbB3   GGVYIEKNDKLCHMDTIDWRDIV---RDADAEIVVKDNGRSCPPCHEVC-KGRCWGPGSE
        *.*  ::.:*  **::::*:*****      :  .: .::   ** *.   * :* ***.*.*

EGFR    NCQKLTKIICAQQCSGRCRGKSPSDCCHNQCAAGCTGPRESDCLVCRKFRDEATCKDTCP
ErbB3   DCQTLTKTICAPQCNGHCFGPNPNQCCHDECAGGCSGPQDTDCFACRHFNDSGACVPRCP
        :**.*** *** **.*:* * .*. :***.:**. ***:** ::**:  .****:**.*. .:*    **

EGFR    PLMLYNPTTYQMDVNPEGKYSFGATCVKKCPRNYVVTDHGSCVRACGADSYEMEEDGVRK
ErbB3   QPLVYNKLTFQLEPNPHTKYQYGGVCVASCPHNFVV-DQTSCVRACPPDKMEVDKNGLKM
        :** *:*:: **. **..*. :****:** *: ****** .*. *::::*::

EGFR    CKRCEGPCRKVCNGIGIGEFKDSLSINATNIKHFKNCTSISGDLHILPVAFRGDSFTHTP
ErbB3   CEPCGGLCPKACEGTGSG--SRFQTVDSSNIDGFVNCTKILGNLDFLITGLNGDPWHKIP
        *:  *  *  *.:* * *  .  ::::**. * ***.* *:.  ...**.:  : *

EGFR    PLDPQELDILKTVKEITGFLLIQAWPENRTDLHAFENLEIIRGRTKQHGQFSLAVV-SLN
ErbB3   ALDPEKLNVFRTVREITGYLNIQSWPPHMHNFSVFSNLTTIGGRSLYNRGFSLLIMKNLN
        .***:*::::**:****:* ***:**  :    :: .*.**  * **:    : *** :: .**

EGFR    ITSLGLRSLKEISDGDVIISGNKNLCYANTINW-KKLFGTSGQKTKIISNRGENSCKATG
ErbB3   VTSLGFRSLKEISAGRIYISANRQLCYHHSLNWTKVLRGPTEERLDIKHNRPRRDCVAEG
        :****:******** *: **.*:*** :::**  * * *.:: :: .* ** ...* * *

EGFR    QVCHALCSPEGCWGPEPRDCVSCRNVSRGRECV
ErbB3   KVCDPLCSSGGCWGPGPGQCLSCRNYSRGGVCV
        :**. ***. ***** * ::**** *** **
```

Fig.1B

```
EGFR    EKKVCQGTSNKLTQLGTFEDHFLSLQRMFNNCEVVLGNLEITYVQRNYDLSFLKTIQEVA
ErbB4   SQSVCAGTENKLSSLSDLEQQYRALRKYYENCEVVMGNLEITSIEHNRDLSFLRSVREVT
        ..:** **.***:.* .*::: :*:: ::*****:****** :::* *****:::.**:

EGFR    GYVLIALNTVERIPLENLQIIRGNMYYENSYALAVLSNYDA-NKTGLKELPMRNLQEILH
ErbB4   GYVLVALNQFRYLPLENLRIIRGTKLYEDRYALAIFLNYRKDGNFGLQELGLKNLTEILN
        ****:*** .. :*****:****. **: ****:: **   .: **:** ::** ***:

EGFR    GAVRFSNNPALCNVESIQWRDIVSSDFLSNMSMDFQNHLGSCQKCDPSCPNGSCWGAGEE
ErbB4   GGVYVDQNKFLCYADTIHWQDIVRNPWPSNLTLVSTNGSSGCGRCHKSC-TGRCWGPTEN
        *.* ..:*  ** ..:*:*:***  . : **::.  * ..:. **.** .* ***. *:

EGFR    NCQKLTKIICAQQCSGRCRGKSPSDCCHNQCAAGCTGPRESDCLVCRKFRDEATCKDTCP
ErbB4   HCQTLTRTVCAEQCDGRCYGPYVSDCCHRECAGGCSGPKDTDCFACMNFNDSGACVTQCP
        :**.**: :**:**.*** *    ******:.**.**:**::.** .* :*.*..:* **

EGFR    PLMLYNPTTYQMDVNPEGKYSFGATCVKKCPRNYVVTDHGSCVRACGADSYEMEEDGVRK
ErbB4   QTFVYNPTTFQLEHNFNAKYTYGAFCVKKCPHNFVV-DSSSCVRACPSSKMEVEENGIKM
        ::*****:*:: * :.**::** ******:*:** * .****** ::. *:**:*::

EGFR    CKKCEGPCRKVCNGIGIGEFKDSLSINATNIKHFKNCTSISGDLHILPVAFRGDSFTHTP
ErbB4   CKPCTDICPKACDGIGTGSLMSAQTVDSSNIDKFINCTKINGNLIFLVTGIHGDPYNAIE
        ** * . * *.:*** *.: .: :::::**.:* ***.*.*:* :* ...::**.:.

EGFR    PLDPQELDILKTVKEITGFLLIQAWPENRTDLHAFENLEIIRGRTKQHGQFSLAVVSLNI
ErbB4   AIDPEKLNVFRTVREITGFLNIQSWPPNMTDFSVFSNLVTIGGRVLYSGLSLLILKQQGI
        .:**::*::::::******* **:** * **:. .* :.**   * *:.. *

EGFR    TSLGLRSLKEISDGDVIISGNKNLCYANTINWKKLFGTSGQKTKIISNRGENSCKATGQV
ErbB4   TSLQFQSLKEISAGNIYITDNSMLCYYHTINWTTLFSTINQRIVIRDNRKAENCTAEGMV
        *** ::****** *:: *:.*.****  :*.**.:**. :*.* .: * .** :.* * *

EGFR    CHALCSPEGCWGPEPRDCVSCRNVSRGRECV
ErbB4   CNHLCSSDGCWGPGPDQCLSCRRFSRGRICI
        *: ***.:***** * :**..**** *:
```

Fig.2B
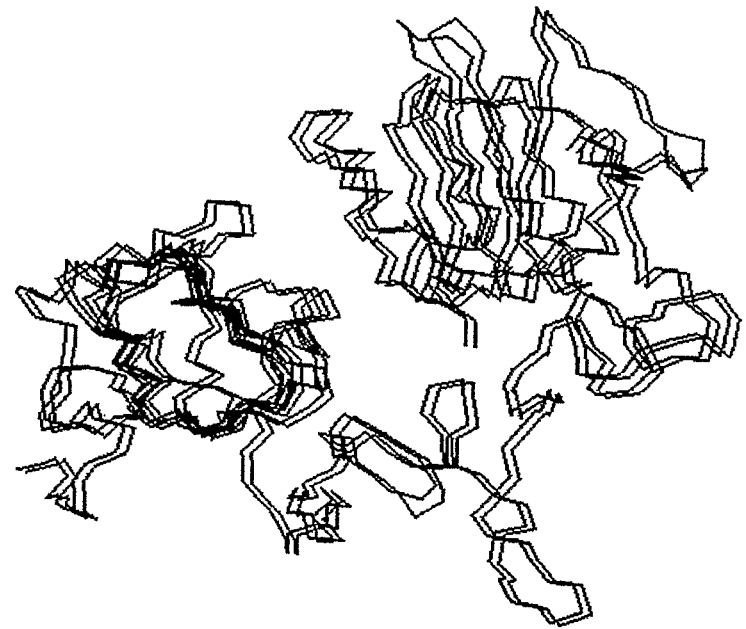
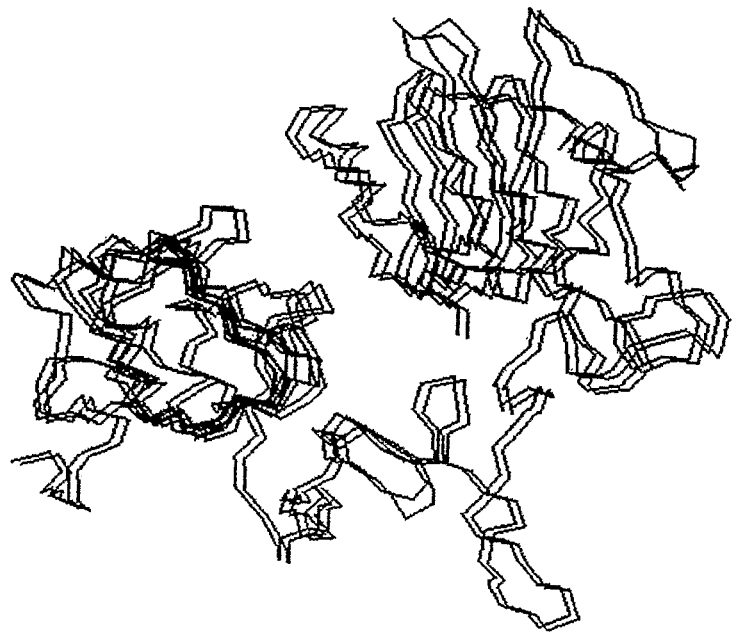

Fig.4A
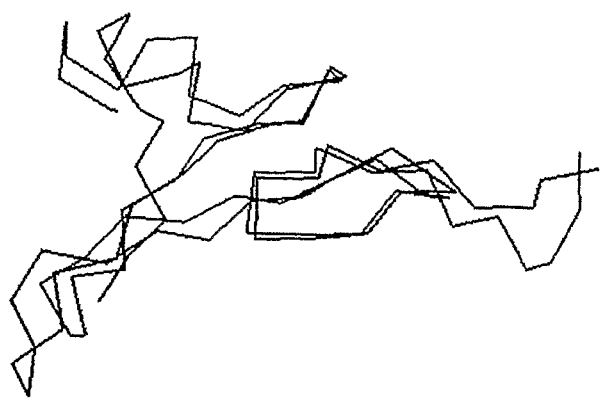
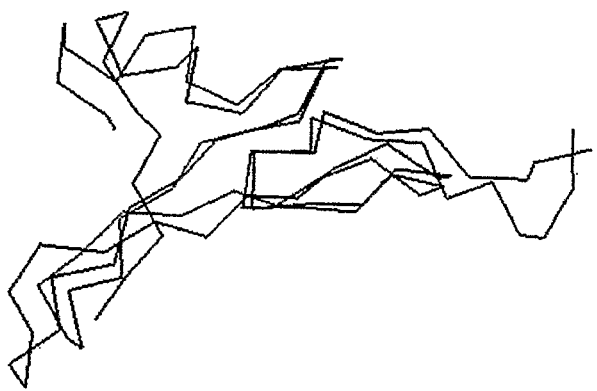

```
            1         10        20        30        40        50
NRG-1β   SHLVKCAEKEKTFCVNGGECFMVKDLSNPSRVLCKCPNEFTGDRCQNYVMAS
hEGF     NSDSECPLSHDGYCLHDGVCMYIEALD--KYACNCVVGYIGERCQYRDLKW
```

NEUREGULIN VARIANTS AND METHODS OF SCREENING AND USING THEREOF

CROSS-REFERENCE TO RELATED APPLICATIONS

This application is a divisional of U.S. application Ser. No. 12/095,904, filed Jun. 2, 2008, which is a 371 U.S. national stage application of PCT/CN2006/003240, having an international filing date of Dec. 4, 2006, which is a continuation-in-part of and claims the benefit of priority of U.S. application Ser. No. 11/293,879 filed Dec. 2, 2005, each of which is incorporated herein by reference in its entirety.

The instant application contains a Sequence Listing which has been submitted in ASCII format via EFS-Web and is hereby incorporated by reference in its entirety. Said ASCII copy, created on Jul. 31, 2013, is named 11748-037-999_SeqList.txt and is 16,885 bytes in size.

FIELD OF THE INVENTION

This invention relates generally to neuregulin variants that selectively activate ErbB receptors. The invention provides neuregulin variants and methods for screening and using such variants.

BACKGROUND OF THE INVENTION

The epidermal growth factor receptor family, which comprises four members EGFR, ErbB2, ErbB3 and ErbB4, has been demonstrated to play an important role in multiple cellular functions, including cell growth, differentiation and survival. They are protein tyrosine kinase receptors, consisting of an extracellular ligand-binding domain, transmembrane domain and cytoplasmic tyrosine kinase domain. Multiple receptor ligands have been identified which mediate receptor homo- or hetero-dimerization upon binding. The specific receptor association results in different patterns of phosphorylation, complex signaling cascades and multiple biological functions, including cellular proliferation, prevention of apoptosis and promotion of tumor cell mobility, adhesion and invasion.

Neuregulin-1 is a ligand of ErbB3 and ErbB4 receptors. Over 15 distinct isoforms of neuregulin-1 have been identified. Neuregulin-1 isoforms can be divided into two large groups, known as α- and β-types, on the basis of differences in the structure of their essential epidermal growth factor (EGF)-like domains. It has been shown that the EGF-like domains of neuregulin-1, ranging in size from 50 to 64-amino acids, are sufficient to bind to and activate these receptors. Previous studies have shown that neuregulin-1β (NRG-1β) can bind directly to ErbB3 and ErbB4 with high affinity. The orphan receptor, ErbB2, holds a pre-activated conformation to facilitate hetero-dimerization with ErbB3 or ErbB4 with approximately 100-fold higher affinity than ErbB3 and ErbB4 homodimers. The heterometric receptors act in distinct cell types: ErbB2/ErbB3 in the peripheral nervous system and ErbB2/ErbB4 in the heart. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1β has been shown to enhance sarcomere organization in adult cardiomyocytes. The short-term administration of a recombinant NRG-1β EGF domain significantly improves or protects against deterioration in myocardial performance in three distinct animal models of heart failure. More importantly, NRG-1β significantly prolongs survival of heart failure animals. These effects make NRG-1β promising as abroad spectrum therapeutic or lead compound for heart failure due to a variety of common diseases. However, there is still a need for detailed structural information of NRG-1β in complex with its receptors for designing variants of NRG-1β for therapeutic use.

Numerous computational studies employing homology modeling, molecular dynamics simulations and free energy calculations have been carried out for ligand-protein and protein-protein interactions at the atomic level. Prediction of absolute ligand-receptor binding free energies is essential in a wide range of biophysical queries such as structure-based drug design. Recently, a new computational approach, the Molecular Mechanics Poisson Boltzmann Surface Area (MM-PBSA), has been used for studying protein-protein interactions. MM-PBSA calculates the free energies of the end states directly to avoid the time-consuming simulation of the intermediate states. This method combines molecular mechanical energies for the solute with a continuum solvent approach and normal mode analysis to estimate the total free energies. Computational alanine-scanning methodology has also been used for studying protein-protein interactions.

BRIEF SUMMARY OF THE INVENTION

In one aspect, the present invention provides a polypeptide variant of neuregulin-1β comprising amino acid sequence shown in SEQ ID NO:1, wherein the polypeptide variant comprises a different amino acid than that in SEQ ID NO:1, wherein the polypeptide variant has an enhanced binding affinity to ErbB3 compared to polypeptide of SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D, E, F, G, H, I, K, L, M, N, P, R, S, T, V, W, or Y.

In some embodiments, the polypeptide variant consists of the amino acid sequence shown in SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D, E, F, G, H, I, K, L, M, N, P, R, S, T, V, W, or Y.

In some embodiments of the polypeptide variants, at residue 25 said different amino acid is A; at residue 35 said different amino acid is A; and/or at residue 46 said different amino acid is A.

In some embodiments, the polypeptide variant has a decreased or similar binding affinity to ErbB4 compared to the polypeptide of SEQ ID NO:1. In some embodiments of the polypeptide variants, at residue 25 said different amino acid is A. In some embodiments of the polypeptide variants, at residue 35 said different amino acid is A. In some embodiments of the polypeptide variants, at residue 46 said different amino acid is A.

The invention also provides a polypeptide variant of neuregulin-1β comprised of amino acid residues 1-52 of SEQ ID NO:1, wherein the polypeptide variant comprises a different amino acid than that in SEQ ID NO:1, wherein the polypeptide variant has an enhanced binding affinity to ErbB3 compared to polypeptide consisting of amino acid residues 1-52 of SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D, E, F, G, H, I, K, L, M, N, P, R, S, T, V, W, or Y.

In some embodiments of the polypeptide variants, at residue 25 said different amino acid is A; at residue 35 said different amino acid is A; and/or at residue 46 said different amino acid is A.

In some embodiments, the polypeptide variant has a decreased or similar binding affinity to an ErbB4 compared to the polypeptide consisting of amino acid residues 1-52 of SEQ ID NO:1. In some embodiments of the polypeptide variants, at residue 25 said different amino acid is A. In some embodiments of the polypeptide variants, at residue 35 said different amino acid is A. In some embodiments of the polypeptide variants, at residue 46 said different amino acid is A.

The invention also provides a polynucleotide comprising a nucleic acid sequence encoding the polypeptide variant described herein that has an enhanced binding affinity to ErbB3 compared to polypeptide of SEQ ID NO:1 or polypeptide consisting of amino acid residues 1-52 of SEQ IN NO:1.

The invention also provides a pharmaceutical composition comprising an effective amount of the polypeptide variant described herein that has an enhanced binding affinity to ErbB3 compared to polypeptide of SEQ ID NO:1 or polypeptide consisting of amino acid residues 1-52 of SEQ IN NO:1, or the polynucleotide encoding the polypeptide variant and a pharmaceutically acceptable excipient.

The invention also provides a kit comprising the pharmaceutical composition. In some embodiments, the kit further comprises an instruction for using the pharmaceutical composition in preventing, treating, or delaying a disease in an individual via activating ErbB2/ErbB3 receptors.

The invention also provides a method for preventing, treating, or delaying development of schizophrenia in a mammal, comprising administering to a mammal, to which such prevention, treatment or delay is needed or desirable, a pharmaceutical composition comprising an effective amount of the pharmaceutical composition. In some embodiments, the mammal is a human.

In another aspect, the present invention provides a polypeptide variant of neuregulin-1β comprising amino acid sequence shown in SEQ ID NO:1, wherein the polypeptide variant comprises a different amino acid than that in SEQ ID NO:1, wherein the polypeptide variant has a decreased binding affinity to ErbB4 compared to polypeptide of SEQ ID NO:1, and wherein at residue 3 said different amino acid is A, C, D, E, F, G, H, I, K, M, N, P, Q, R, S, T, V, W, or Y.

In some embodiments, the polypeptide variant consists of the amino acid sequence shown in SEQ ID NO:1, and wherein at residue 3 said different amino acid is A, C, D, E1 F, G, H, I, K, M, N, P, Q, R, S, T, V, W, or Y.

In some embodiments of the polypeptide variants, at residue 3 said different amino acid is A.

In some embodiments, the polypeptide variant has an increased or similar binding affinity to ErbB3 compared to the polypeptide of SEQ ID NO:1. In some embodiments of the polypeptide variants, at residue 3 said different amino acid is A.

The invention also provides a polypeptide variant of neuregulin-1β comprised of amino acid residues 1-52 of SEQ ID NO:1, wherein the polypeptide variant comprises a different amino acid than that in SEQ ID NO:1, wherein the polypeptide variant has a decreased binding affinity to ErbB4 compared to polypeptide consisting of amino acid residues 1-52 of SEQ ID NO:1, and wherein at residue 3 said different amino acid is A, C, D, E, F, G, H, I, K, M, N, P, Q, R, S, T, V, W, or Y.

In some embodiments of the polypeptide variants, at residue 3 said different amino acid is A.

In some embodiments, the polypeptide variant has an enhanced or similar binding affinity to an ErbB3 compared to the polypeptide consisting of amino acid residues 1-52 of SEQ ID NO:1. In some embodiments of the polypeptide variants, at residue 3 said different amino acid is A.

The invention also provides a polynucleotide comprising a nucleic acid sequence encoding the polypeptide variant described herein that has a decreased binding affinity to ErbB4 compared to polypeptide of SEQ ID NO:1 or polypeptide consisting of amino acid residues 1-52 of SEQ ID NO:1.

The invention also provides a pharmaceutical composition comprising an effective amount of the polypeptide variant described herein that has a decreased binding affinity to ErbB4 compared to polypeptide of SEQ ID NO:1 or polypeptide consisting of amino acid residues 1-52 of SEQ IN NO:1, or the polynucleotide encoding the polypeptide variant and a pharmaceutically acceptable excipient.

The invention also provides a kit comprising the pharmaceutical composition. In some embodiments, the kit further comprises an instruction for using the pharmaceutical composition in preventing, treating, or delaying a disease in an individual via activating ErbB2/ErbB3.

The invention also provides a method for preventing, treating, or delaying development of schizophrenia in a mammal, comprising administering to a mammal, to which such prevention, treatment or delay is needed or desirable, a pharmaceutical composition comprising an effective amount of the pharmaceutical composition. In some embodiments, the mammal is a human.

In another aspect, the present invention provides a polypeptide variant of neuregulin-1β comprising amino acid sequence shown in SEQ ID NO:1, wherein the polypeptide variant comprises a different amino acid than that in SEQ ID NO:1, wherein the polypeptide variant has an enhanced binding affinity to ErbB4 compared to polypeptide of SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y.

In some embodiments, the polypeptide variant consists of the amino acid sequence shown in SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y.

In some embodiments of the polypeptide variants, at residue 16 said different amino acid is A; at residue 29 said different amino acid is A; at residue 31 said different amino acid is A; at residue 43 said different amino acid is A; or at residue 47 said different amino acid is A.

In some embodiments, the polypeptide variant has a decreased or similar binding affinity to an ErbB3 compared to the polypeptide of SEQ ID NO:1. In some embodiments of the polypeptide variants, at residue 31 said different amino acid is A. In some embodiments of the polypeptide variants, at residue 43 said different amino acid is A. In some embodiments of the polypeptide variants, at residue 47 said different amino acid is A.

The invention also provides a polypeptide variant of neuregulin-1β consisting of amino acid residues 1-52 of SEQ ID NO:1, wherein the polypeptide variant comprises a different amino acid than that in SEQ ID NO:1, wherein the polypeptide variant has an enhanced binding affinity to ErbB4 compared to polypeptide consisting of amino acid residues 1-52 of SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y.

In some embodiments of the polypeptide variants, at residue 16 said different amino acid is A; at residue 29 said different amino acid is A; at residue 31 said different amino acid is A; at residue 43 said different amino acid is A; and/or at residue 47 said different amino acid is A.

In some embodiments, the polypeptide variant has a decreased or similar binding affinity to an ErbB3 compared to the polypeptide of SEQ ID NO:1. In some embodiments of the polypeptide variants, at residue 31 said different amino acid is A. In some embodiments of the polypeptide variants, at residue 43 said different amino acid is A. In some embodiments of the polypeptide variants, at residue 47 said different amino acid is A.

The invention also provides a polypeptide variant of neuregulin-1β comprising amino acid sequence of SEQ ID NO:1, wherein the polypeptide variant comprises a different amino acid than that in SEQ ID NO:1, wherein the polypeptide variant has a decreased binding affinity to EirbB3 compared to polypeptide of SEQ ID NO:1 but has a binding affinity to ErbB4 similar to polypeptide of SEQ ID NO:1, and wherein at residue 33 said different amino acid is A.

The invention also provides a polypeptide variant of neuregulin-1β consisting of amino acid residues 1-52 of SEQ ID NO: 1, wherein the polypeptide variant, comprises a different amino acid than that in SEQ ID NO:1, wherein the polypeptide variant has a decreased binding affinity to ErbB3 compared to polypeptide consisting of amino acid residues 1-52 of SEQ ID NO:1 but has a binding affinity to ErbB4 similar to polypeptide consisting of amino acid residues 1-52 SEQ ID NO:1, and wherein at residue 33 said different amino acid is A.

The invention also provides a polynucleotide comprising a nucleic acid sequence encoding the polypeptide variant described herein that has an enhanced binding affinity to ErbB4 compared to polypeptide of SEQ ID NO:1 or polypeptide consisting of amino acid residues 1-52 of SEQ ID NO:1.

The invention also provides a pharmaceutical composition comprising an effective amount of the polypeptide variant described herein that has an enhanced binding affinity to ErbB4 compared to polypeptide of SEQ ID NO:1 or polypeptide consisting of amino acid residues 1-52 of SEQ ID NO:1, or the polynucleotide encoding the polypeptide variant and a pharmaceutically acceptable excipient.

The invention also provides a kit comprising the pharmaceutical composition. In some embodiments, the kit further comprises an instruction for using the pharmaceutical composition in preventing, treating, or delaying a disease in an individual via activating ErbB2/ErbB4 receptors.

The invention also provides a method for preventing, treating, or delaying development of viral myocarditis, dilated (congestive) cardiomyopathy, cardiac toxicity, heart failure, myocardial infarction in an individual, comprising administering to an individual, to which such prevention, treatment or delay is needed or desirable, a pharmaceutical composition comprising an effective amount of the pharmaceutical composition. In some embodiments, the mammal is a human.

In another aspect, the invention provides a method for screening a polypeptide variant of neuregulin-1β having enhanced binding affinity to ErbB3, which method comprises: (a) establishing a three-dimensional structure of a neuregulin-1β or a fragment thereof, an ErbB3, and a complex of the neuregulin-1β or the fragment thereof and the ErbB3 by homology modeling; (b) establishing data of conformational changes and stability of the complex of the neuregulin-1β or the fragment thereof and the ErbB3 in solution by molecular dynamics simulation method; (c) calculating subtotal binding free energy ($\Delta G_{subtotal\ wildtype}$) of the neuregulin-1β or the fragment thereof with the ErbB3 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 by Molecular Mechanics Poisson Boltzmann Surface Area (MM-PBSA) method, wherein the alanine substituted variant comprises an amino acid of the neuregulin-1β or the fragment thereof substituted, by an alanine; (e) calculating $\Delta\Delta G_{subtotal} = \Delta G_{subtotal\ wildtype} - \Delta G_{subtotal\ alanine\ substituted\ variant}$; and (f) selecting alanine substituted variant that has a positive value of $\Delta\Delta G_{subtotal}$ for the complex of the neuregulin-1β or the fragment thereof and the ErbB3; whereby a polypeptide variant of neuregulin-1β that has enhanced binding affinity to ErbB3 is identified.

The invention also provides a method for screening a polypeptide variant of neuregulin-1β having enhanced binding affinity selective to ErbB3, which method comprises: (a) establishing a three-dimensional structure of a neuregulin-1β or a fragment thereof, an ErbB3, an ErbB4, a complex of the neuregulin-1β or the fragment thereof and the ErbB3, and a complex of the neuregulin-1β or the fragment thereof and the ErbB4 by homology modeling; (b) establishing data of conformational changes and stability of the complex of the neuregulin-1β or the fragment thereof and the ErbB3, and the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB3 or the ErbB4 by Molecular Mechanics Poisson Boltzmann Surface Area (MM-PBSA) method; (d) calculating subtotal binding free energy ($\Delta_{subtotal\ alanine\ substituted\ variant}$) of an alanine substituted variant of the neuregulin-1β or the fragment thereof with the ErbB3 or the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} \Delta G_{subtotal\ alanine\ substituted\ variant}$; (f) selecting alanine substituted variant that has a positive value of $\Delta\Delta G_{subtotal}$ for the complex of the neuregulin-1β or the fragment thereof and the ErbB3, and has a negative value or a value of about zero for $\Delta\Delta G_{subtotal}$ for the complex of the neuregulin-1β or the fragment thereof and the ErbB4; whereby a polypeptide variant of neuregulin-1β that has enhanced binding affinity selective to ErbB3 is identified. In some embodiments, an alanine substituted variant having the negative value for $\Delta\Delta G_{subtotal}$ for the complex of the neuregulin-1β or the fragment thereof and the ErbB4 is selected, whereby a polypeptide variant of neuregulin-1β that has enhanced binding affinity to ErbB3 but decreased binding affinity to ErbB4 is identified. In some embodiments, an alanine substituted variant having the value of about zero for $\Delta\Delta G_{subtotal}$ for the complex of the neuregulin-1β or the fragment thereof and the ErbB4 is selected, whereby a polypeptide variant of neuregulin-1β that has enhanced binding affinity to ErbB3 but unchanged binding affinity to ErbB4 is identified.

In another aspect, the invention provides a method for screening a polypeptide variant of neuregulin-1β having enhanced binding affinity to ErbB4, which method comprises: (a) establishing a three-dimensional structure of a neuregulin-1β or a fragment thereof, an ErbB4, and a complex of the neuregulin-1β or the fragment thereof and the ErbB4 by homology modeling; (b) establishing data of conformational changes and stability of the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB4 by Molecular Mechanics Poisson Boltzmann Surface Area (MM-PBSA) method; (d) calculating subtotal binding free energy ($<G_{subtotal\ alanine\ substituted\ variant}$) of an alanine substituted variant of the neuregulin-1β or the fragment thereof with the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; and (f) selecting an alanine substituted variant that has a positive value of $\Delta\Delta G_{subtotal}$ for the complex of the neuregulin-1β or the fragment thereof and the ErbB4; whereby a polypeptide variant of neuregulin-1β that has enhanced binding affinity to ErbB4 is identified.

The invention also provides a method for screening a polypeptide variant of neuregulin-1β having enhanced binding affinity selective to ErbB4, which method comprises: (a) establishing a three-dimensional structure of a neuregulin-1β or a fragment thereof, an ErbB3, an ErbB4, a complex of the neuregulin-1β or the fragment thereof and the ErbB3, and a complex of the neuregulin-1β or the fragment thereof and the ErbB4 by homology modeling; (b) establishing data of conformational changes and stability of the complex of the neuregulin-1β or the fragment thereof and the ErbB3, and the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB3 or the ErbB4 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 or the ErbB4 by Molecular Mechanics Poisson Boltzmann Surface Area (MM-PBSA) method, wherein the alanine substituted variant, comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; (f) selecting alanine substituted variant that has a positive value of $\Delta\Delta G_{subtotal}$ for the complex of the neuregulin-1β or the fragment thereof and the ErbB4, and has a negative value or a value of about zero for $\Delta\Delta G_{subtotal}$ for the complex of the neuregulin-1β or the fragment thereof and the ErbB3; whereby a polypeptide variant of neuregulin-1β that has enhanced binding affinity selective to ErbB4 is identified. In some embodiments, alanine substituted variant having the negative value for $\Delta\Delta G_{subtotal}$ for the complex of the neuregulin-1β or the fragment thereof and the ErbB3 is selected, whereby a polypeptide variant of neuregulin-1β that has enhanced binding affinity to ErbB4 but decreased binding affinity to ErbB3 is identified. In some embodiments, alanine substituted variant having the value of about zero for $\Delta\Delta G_{subtotal}$ for the complex of the neuregulin-1β or the fragment thereof and the ErbB3 is selected, whereby a polypeptide variant of neuregulin-1β that has enhanced binding affinity to ErbB4 but unchanged binding affinity to ErbB3 is identified.

The invention also provides a method for screening a polypeptide variant of neuregulin-1β having unchanged binding affinity to ErbB4 but has decreased binding affinity to ErbB3, which method comprises: (a) establishing a three-dimensional structure of a neuregulin-1β or a fragment thereof, an ErbB3, an ErbB4, a complex of the neuregulin-1β or the fragment thereof and the ErbB3, and a complex of the neuregulin-1β or the fragment thereof and the ErbB4 by homology modeling; (b) establishing data of conformational changes and stability of the complex of the neuregulin-1β or the fragment thereof and the ErbB3, and the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB3 or the ErbB4 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 or the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; (f) selecting alanine substituted variant that has a value of about zero for $\Delta\Delta G_{subtotal}$ for the complex of the neuregulin-1β or the fragment thereof and the ErbB4 and has a negative value, for $\Delta\Delta G_{subtotal}$ for the complex of the neuregulin-1β or the fragment thereof and the ErbB3; whereby a polypeptide variant of neuregulin-1β that has unchanged binding affinity to ErbB4 but has decreased binding affinity to ErbB3 is identified.

The invention also provides a polypeptide variant of a neuregulin-1β identified by the methods described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B show a pairwise alignment between (FIG. 1A) ErbB3 (SEQ ID NO: 6) and EGFR (SEQ ID NO:5), and (FIG. 1B) ErbB4 (SEQ ID NO:7) and EGFR (SEQ ID NO:5) used for homology modeling. In the sequence, "*" refers to identical residues; ":" refers to conservative substitutions; and "." refers to semi-conservative substitutions. The boxes indicate structurally conserved regions.

FIGS. 2A and 2B show stereo views of refined receptor (FIG. 2A) ErbB3 (blue) and (FIG. 2B) ErbB4 (blue) Cα traces superimposed on the x-ray structure of EGFR (red).

FIGS. 4A and 4B show stereo views of (FIG. 4A) the best fit superposition of Cα atoms of the minimized NRG-1β (SEQ ID NO:8) coordinates (blue) on EGF (SEQ ID NO:9) (red) and (FIG. 4B) the aligned amino acid sequences of these proteins.

FIG. 5 shows root mean square deviations for the Cα atoms during the dynamics simulations of complexes of ErbB3 (dash lines) and ErbB4 (solid lines) with NRG-1β.

(FIG. 6B) the interface at site 2; (FIG. 6C) the interface at site 3. Only the side chains of interacting residues are shown. Dotted lines represent hydrogen bonds.

(FIG. 7B) the interface at site 2; (FIG. 7C) the interface at site 3. Only the side chains of interacting residues are shown. Dotted lines represent hydrogen bonds.

(FIG. 8B) the binding energy change for the computational alanine scanning mutagenesis experiments for ErbB4 complex with NRG-1β. Negative values in $\Delta\Delta G_{subtotal}$ indicate highly unfavorable substitutions. Positive values in $\Delta\Delta G_{subtotal}$ indicate the preference alanine mutations for the residues.

DETAILED DESCRIPTION OF THE INVENTION

Figure 2A:

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "neuregulin" or "NRG" refers to proteins or peptides that can bind and activate ErbB2/ErbB4 or ErbB2/ErbB3 heterodimers protein kinases, such as all neuregulin isoforms, neuregulin EGF domain alone, neuregulin mutants, and any kind of neuregulin-like gene products that also activate the above receptors. Neuregulin also includes NRG-1, NRG-2, NRG-3, and NRG-4. These proteins and polypeptides can activate the above ErbB receptors and modulate their biological reactions, e.g., stimulate breast cancer cell differentiation and milk protein secretion; induce the differentiation of neural crest cell into Schwann cell; stimulate acetylcholine synthesis in skeletal muscle cell; and improve cardiocyte survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Bejacrrim/Cummings Pub. co., p. 224). Neuregulin protein encompasses a neuregulin protein and peptide. Neuregulin nucleic acid encompasses neuregulin nucleic acid and neuregulin oligonucleotide.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256:1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochern., 122:675-680 (1997); and WO 97/09425. EGF-like domains may be derived from NRG-1, NRG-1, NRG-3, or NRG-4. EGF-like domains may be α or β subtype.

As used herein, a "functional derivative or fragment" of neuregulin refers to a derivative or fragment of the neuregulin protein or its encoding nucleic acid that still substantially retains its anti-viral myocarditis, anti-DCM, anti-cardiotoxic, or antimyocardial infarction activity. Normally, the derivative or fragment retains at least 50% of its anti-viral myocarditis, anti-DCM, anti-cardiotoxic, or anti-myocardial infarction activity. Preferably, the derivative or fragment retains at least 60%, 70%, 80%, 90%, 95%, 99% and 100% of its anti-viral myocarditis, anti-DCM, anti-cardiotoxic, or anti-myocardial infarction activity.

As used herein, "erb" refers to two oncogenes, erb A and erb B, associated with erythroblastosis virus (an acute transforming retrovirus).

As used herein, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "treatment" or "treating" refer to any manner in which the symptoms of a condition, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, "production by recombinant means" refers to production methods that use recombinant nucleic acid methods that rely on well known methods of molecular biology for expressing proteins encoded by cloned nucleic acids.

As used herein, "complementary" when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:
1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.
It is understood that equivalent stringencies may be achieved using alternative buffers, salts and temperatures.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

As used herein, "myocardial infarction" refers to a blockade of a coronary artery or blood flow interruption leading to focal necrosis of part of the myocardium caused by severe and persistent ischemia.

B. NRG-1β VARIANTS AND PHARMACEUTICAL COMPOSITIONS

The present invention provides polypeptide variants of NRG-1 polynucleotide encoding the polypeptide variants and pharmaceutical compositions.

A functional human NRG-1 fragment has the amino acid sequence: Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe Tyr Lys Ala Glu Glu Leu Tyr Gln (SEQ ID NO:1) which corresponds to amino acids 177-237 of human NRG-1.

The human nucleic acid sequence encoding the fragment is agccatcttg taaaatgtgc ggagaaggag aaaactttct gtgtgaatgg agggagtgc ttcatggtga aagacctttc aaacccctcg agatacttgt gcaagtgccc aaatgagttt actggtgatc gctgccaaaa ctacgtaatg gcgagcttct acaaggcgga ggagctgtac cag (SEQ ID NO:2).

The present invention provides for neuregulin1β variants that comprise amino acid sequence of SEQ ID NO:1 and comprise a different amino acid than that in SEQ ID NO:1 at residue 3, 8, 16, 25, 29, 31, 33, 35, 43, 46, or 47. In certain embodiments, neuregulin1β variants of the present invention contain a single amino acid substitute at residue 3, 8, 16, 25, 29, 31, 33, 35, 43, 46, or 47 of SEQ ID NO:1. In certain embodiments, neuregulin1β variants of the present invention contain multiple amino acid substitutions at residue 3, 8, 16, 25, 29, 31, 33, 35, 43, 46, or 47 of SEQ ID NO:1. In some embodiments, neuregulin1β variants of the present invention contain two, three, four, five or six amino acid substitutions at residue 3, 8, 16, 25, 29, 31, 33, 35, 43, 46, or 47 of SEQ ID 1N0:1.

In one aspect, the present invention is directed to a polypeptide variant of neuregulin-1β comprising amino acid sequence shown in SEQ ID NO:1, wherein the polypeptide variant comprises a different amino acid than that in SEQ ID NO:1, wherein the polypeptide variant has an enhanced binding affinity to ErbB3 compared to polypeptide of SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D; E, F, G, H, I, K, L, M, N, P, R, S, T, V, W, or Y.

In some embodiments, the polypeptide variant consists of the amino acid sequence shown in SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D, E, F, G, H, I, K, L, M, N, P, R, S, T, V, W, or Y, In some embodiments of the polypeptide variants, at residue 25 said different amino acid is A; at residue 35 said different amino acid is A; and/or at residue 46 said different amino acid is A.

In some embodiments, the polypeptide variant has a decreased or similar affinity to an ErbB4 compared to the polypeptide of SEQ ID NO:1. In some embodiments of the polypeptide variants, at residue 25 said different amino acid is A. In some embodiments of the polypeptide variants, at residue 35 said different amino acid is A. In some embodiments of the polypeptide variants, at residue 46 said different amino acid is A.

The invention also provides a polypeptide variant of neuregulin-1β consisting of amino acid residues 1-52 of SEQ ID NO:1, wherein the polypeptide variant comprises a different amino acid than that in SEQ ID NO:1, wherein the polypeptide variant has an enhanced binding affinity to ErbB3 compared to polypeptide consisting of amino acid residues 1-52 of SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D, E, F, G, H, I, K, L, M, N, P, R, S, T, V, W, or Y.

In some embodiments of the polypeptide variants, at residue 25 said different amino acid is A; at residue 35 said different amino acid is A; and/or at residue 46 said different amino acid is A.

In some embodiments, the polypeptide variant has a decreased or similar binding affinity to an ErbB4 compared to the polypeptide consisting of amino acid residues 1-52 of SEQ ID NO:1. In some embodiments of the polypeptide variants, at residue 25 said different amino acid is A. In some embodiments of the polypeptide variants, at residue 35 said different amino acid is A. In some embodiments of the polypeptide variants, at residue 46 said different amino acid is A.

In another aspect, the present invention provides a polypeptide variant of neuregulin-1β comprising amino acid sequence shown in SEQ ID NO:1, wherein the polypeptide variant comprises a different amino acid than that in SEQ ID NO:1, wherein the polypeptide variant has a decreased binding affinity to ErbB4 compared to polypeptide of SEQ ID NO:1, and wherein at residue 3 said different amino acid is A, C, D, E, F, G, H, I, K, M, N, P, Q, R, S, T, V, W, or Y.

In some embodiments, the polypeptide variant consists of the amino acid sequence shown in SEQ ID NO:1, and wherein at residue 3 said different amino acid is A, C, D, E, F, G, H, I, K, M, N, P, Q, R, S, T, V, W, or Y.

In some embodiments of the polypeptide variants, at residue 3 said different amino acid is A.

In some embodiments, the polypeptide variant has an increased or similar binding affinity to ErbB3 compared to the polypeptide of SEQ ID NO:1. In some embodiments of the polypeptide variants, at residue 3 said different amino acid is A.

The invention also provides a polypeptide variant of neuregulin-1β comprised of amino acid residues 1-52 of SEQ ID NO:1, wherein the polypeptide variant comprises a different amino acid than that in SEQ ID NO:1, wherein the polypeptide variant has a decreased binding affinity to ErbB4 compared to polypeptide consisting of amino acid residues 1-52 of SEQ ID NO:1, and wherein at residue 3 said different amino acid is A, C, D, E, F, G, H, I, K, M, N, P, Q, R, S, T, V, W, or Y.

In some embodiments of the polypeptide variants, at residue 3 said different amino acid is A.

In some embodiments, the polypeptide variant has an enhanced or similar binding affinity to an ErbB3 compared to the polypeptide consisting of amino acid residues 1-52 of SEQ ID NO:1. In some embodiments of the polypeptide variants, at residue 3 said different amino acid is A.

The invention also provides a polynucleotide comprising a nucleic acid sequence encoding the polypeptide variant described herein that has a decreased binding affinity to ErbB4 compared to polypeptide of SEQ ID NO:1 or polypeptide consisting of amino acid residues 1-52 of SEQ IN NO:1.

The invention also provides a pharmaceutical composition comprising an effective amount of the polypeptide variant described herein that has a decreased binding affinity to ErbB4 compared to polypeptide of SEQ ID NO:1 or polypeptide consisting of amino acid residues 1-52 of SEQ IN NO:1, or the polynucleotide encoding the polypeptide variant and a pharmaceutically acceptable excipient.

The invention also provides a kit comprising the pharmaceutical composition. In some embodiments, the kit further comprises an instruction for using the pharmaceutical composition in preventing, treating, or delaying a disease in an individual via activating ErbB2/ErbB3.

The invention also provides a polypeptide variant of neuregulin-1β comprising amino acid sequence shown in SEQ ID NO:1, wherein the polypeptide variant comprises a different amino acid than that in SEQ ID NO:1, wherein the polypeptide variant has an enhanced binding affinity to ErbB4 compared to polypeptide of SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y.

In some embodiments, the polypeptide variant consists of the amino acid sequence shown in SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y.

In some embodiments of the polypeptide variants, at residue 16 said different amino acid is A; at residue 29 said different amino acid is A; at residue 31 said different amino acid is A; at residue 43 said different amino acid is A; or at residue 47 said different amino acid is A.

In some embodiments, the polypeptide variant has a decreased or similar binding affinity to an ErbB3 compared to the polypeptide of SEQ ID NO:1. In some embodiments of the polypeptide variants, at residue 31 said different amino acid is A. In some embodiments of the polypeptide variants, at residue 43 said different amino acid is A. In some embodiments of the polypeptide variants, at residue 47 said different amino acid is A.

The invention also provides a polypeptide variant of neuregulin-1β consisting of amino acid residues 1-52 of SEQ ID NO:1, wherein the polypeptide variant comprises a different amino acid than that in SEQ ID NO:1, wherein the polypeptide variant has an enhanced binding affinity to ErbB4 compared to polypeptide consisting of amino acid residues 1-52 of SEQ ID NO 1; and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, R, Q, S, T, V, W, or Y; and/or at residue 47 said different amino acid is A, C, D, E, F, G, H, I, K, L, M, P, Q, R, S, T, V, W, or Y.

In some embodiments of the polypeptide variants, at residue 16 said different amino acid is A; at residue 29 said different amino acid is A; at residue 31 said different amino acid is A; at residue 43 said different amino acid is A; or at residue 47 said different amino acid is A.

In some embodiments, the polypeptide variant has a decreased or similar binding affinity to an ErbB3 compared to the polypeptide of SEQ ID NO:1. In some embodiments of the polypeptide variants, at residue 31 said different amino acid is A. In some embodiments of the polypeptide variants, at residue 43 said different amino acid is A. In some embodiments of the polypeptide variants, at residue 47 said different amino acid is A.

The invention also provides a polypeptide variant of neuregulin-1β comprising amino acid sequence of SEQ ID NO:1, wherein the polypeptide variant comprises a different amino acid than that in SEQ ID NO:1, wherein the polypeptide variant has a decreased binding affinity to ErbB3 compared to polypeptide of SEQ ID NO:1 but has a binding affinity to ErbB4 similar to polypeptide of SEQ ID NO:1, and wherein at residue 33 said different amino acid is A.

The invention also provides a polypeptide variant of neuregulin-1β consisting of amino acid residues 1-52 of SEQ ID NO:1, wherein the polypeptide variant comprises a different amino acid than that in SEQ ID NO:1, wherein the polypeptide variant has a decreased binding affinity to ErbB3 compared to polypeptide consisting of amino acid residues 1-52 of SEQ ID NO:1 but has a binding affinity to ErbB4 similar to polypeptide consisting of amino acid residues 1-52 SEQ ID NO:1, and wherein at residue 33 said different amino acid is A.

The polypeptides of the invention may be produced by chemical synthesis or recombinant methods. Methods of chemically synthesizing polypeptides are well known in the art. Synthesizing polypeptides using recombinant methods are also well known in the art and are further described herein. The polypeptides generated may be tested for their binding affinity to the receptor and activation of the receptor using methods known in the art.

The invention also provides a polynucleotide comprising a nucleic acid sequence encoding any of the polypeptide variants described herein. Polynucleotides complementary to any of the sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. The polynucleotides of this invention can be obtained using chemical synthesis, recombinant methods, or PCR.

It will be appreciated by those of ordinary skill in the art that, as a result of the degeneracy of the genetic code, there are many nucleotide sequences that encode a polypeptide as described herein. Polynucleotides that vary due to differences in codon usage are specifically contemplated by the present invention.

The polynucleotides described herein may be cloned into vectors (such as expression vectors) and transfected into host cells for production of the polypeptides. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication: one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Examples of mammalian host cells include, but are not limited to, COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

The invention also provides pharmaceutical compositions comprising any of the polypeptide variants of NRG-1 or polynucleotides encoding the polypeptide variants described herein and a pharmaceutically acceptable excipient or carrier. As used herein, "pharmaceutically acceptable excipient or carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000). Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of the polypeptide and the polynucleotide being administered.

C. METHODS OF SCREENING POLYPEPTIDE VARIANTS OF NRG-1β

The present invention also provides methods of screening polypeptide variants of NRG-1. For example, solvent-equilibrated models of the NRG-1β/ErbB3 and NRG-1β/ErbB4 complexes can be constructed using an EGF/EGFR co-crystal structure (see Ogiso, H., et al., Crystal structure of the complex of human epidermal growth factor and receptor extracellular domains. Cell 110, 775-787 (2002), the contents of which are incorporated by reference), as a starting point, due to the high homology of this ligand and receptor family. Detailed analysis of the atomic interactions between the interfaces of NRG-1β/ErbB3 and NRG-1β/ErbB4 is then conducted. The MM-PBSA method is used to calculate the free energies for the binding of ErbB3 and ErbB4 to NRG-1β. In addition, computational alanine-scanning mutagenesis of selected residues in the binding-site is performed to rationalize the affinities of the two receptors to NRG-1β. The created computational models of NRG-1β/ErbB3 and NRG-1β/ErbB4 should enable design of NRG-1β variants with enhanced affinity and selectivity for ErbB4, thus improving their therapeutic properties.

The invention provides a method for screening a polypeptide variant of neuregulin-1β having enhanced binding affinity to ErbB3, which method comprises: (a) establishing a three-dimensional structure of a neuregulin-1β or a fragment thereof, an ErbB3, and a complex of the neuregulin-1β or the fragment thereof and the ErbB3 by homology modeling; (b) establishing data of conformational changes and stability of the complex of the neuregulin-1β or the fragment thereof and the ErbB3 in solution by molecular dynamics simulation method; (c) calculating subtotal binding free energy ($\Delta G_{subtotal\ wildtype}$) of the neuregulin-1β or the fragment thereof with the ErbB3 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; and (f) selecting alanine substituted variant that has a positive value of $\Delta\Delta G_{subtotal}$ for the complex of the neuregulin-1β or the fragment thereof and the ErbB3; whereby a polypeptide variant of neuregulin-1β that has enhanced binding affinity to ErbB3 is identified.

The invention also provides a method for screening a polypeptide variant of neuregulin-1β having enhanced binding affinity selective to ErbB3, which method comprises: (a) establishing a three-dimensional structure of a neuregulin-1β or a fragment thereof, an ErbB3, an ErbB4, a complex of the neuregulin-1β or the fragment thereof and the ErbB3, and a complex of the neuregulin-1β or the fragment thereof and the ErbB4 by homology modeling; (b) establishing data of conformational changes and stability of the complex of the neuregulin-1β or the fragment thereof and the ErbB3, and the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB3 or the ErbB4 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 or the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; (f) selecting alanine substituted variant that has a positive value of $\Delta\Delta G_{subtotal}$ for the complex of the neuregulin-1β or the fragment thereof and the ErbB3, and has a negative value or a value of about zero for $\Delta\Delta G_{subtotal}$ for the complex of the neuregulin-1β or the fragment thereof and the ErbB4; whereby a polypeptide variant of neuregulin-1β that has enhanced binding affinity selective to ErbB3 is identified. In some embodiments, alanine substituted variant having the negative value for $\Delta\Delta G_{subtotal}$ for the complex of the neuregulin-1β or the fragment thereof and the ErbB4 is selected, whereby a polypeptide variant of neuregulin-1β that has enhanced binding affinity to ErbB3 but decreased binding affinity to ErbB4 is identified. In some embodiments, an alanine substituted variant having the value of about zero for $\Delta\Delta G_{subtotal}$ for the complex of the neuregulin-1β or the fragment thereof and the ErbB4 is selected, whereby a polypeptide variant of neuregulin-1β that has enhanced binding affinity to ErbB3 but unchanged binding affinity to ErbB4 is identified.

In another aspect, the invention provides a method for screening a polypeptide variant of neuregulin-1β having enhanced binding affinity to ErbB4, which method comprises: (a) establishing a three-dimensional structure of a neuregulin-1β or a fragment thereof, an ErbB4, and a complex of the neuregulin-1β or the fragment thereof and the ErbB4 by homology modeling; (b) establishing data of conformational changes and stability of the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB4 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; and (f) selecting alanine substituted variant that has a positive value of $\Delta\Delta G_{subtotal}$ for the complex of the neuregulin-1β or the fragment, thereof and the ErbB 4; whereby a polypeptide variant of neuregulin-1β that has enhanced binding affinity to ErbB4 is identified.

The invention also provides a method for screening a polypeptide variant of neuregulin-1β having enhanced binding affinity selective to ErbB4, which method comprises: (a)

establishing a three-dimensional structure of a neuregulin-1β or a fragment thereof, an ErbB3, an ErbB4, a complex of the neuregulin-1β or the fragment thereof and the ErbB3, and a complex of the neuregulin-1β or the fragment thereof and the ErbB4 by homology modeling; (b) establishing data of conformational changes and stability of the complex of the neuregulin-1β or the fragment thereof and the ErbB3, and the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB3 or the ErbB4 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 or the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; (f) selecting alanine substituted variant that has a positive value of $\Delta\Delta G_{subtotal}$ for the complex of the neuregulin-1β or the fragment thereof and the ErbB4, and has a negative value or a value of about zero for $\Delta\Delta G_{subtotal}$ for the complex of the neuregulin-1β or the fragment thereof and the ErbB3; whereby a polypeptide variant of neuregulin-1β that has enhanced binding affinity selective to ErbB4 is identified. In some embodiments, an alanine substituted variant having a negative value for $\Delta\Delta G_{subtotal}$ for the complex of the neuregulin-1β or the fragment thereof and the ErbB3 is selected, whereby a polypeptide variant of neuregulin-1β that has enhanced binding affinity to ErbB4 but decreased binding affinity to ErbB3 is identified. In some embodiments, an alanine substituted variant having the value of about zero for $\Delta\Delta G_{subtotal}$ for the complex of the neuregulin-1β or the fragment thereof and the ErbB3 is selected, whereby a polypeptide variant of neuregulin-1β that has enhanced binding affinity to ErbB4 but unchanged binding affinity to ErbB3 is identified.

The invention also provides a method for screening a polypeptide variant of neuregulin-1β having unchanged binding affinity to ErbB4 but has decreased binding affinity to ErbB3, which method comprises: (a) establishing a three-dimensional structure of a neuregulin-1β or a fragment thereof, an ErbB3, an ErbB4, a complex of the neuregulin-1β or the fragment thereof and the ErbB3, and a complex of the neuregulin-1β or the fragment thereof and the ErbB4 by homology modeling; (b) establishing data of conformational changes and stability of the complex of the neuregulin-1β or the fragment thereof and the ErbB3, and the complex of the neuregulin-1β or the fragment thereof and the ErbB4 in solution by molecular dynamics simulation method; (c) calculating subtotal binding free energy ($\Delta G_{subtotal\ wildtype}$) of the neuregulin-1β or the fragment thereof with the ErbB3 or the ErbB4 by Molecular Mechanics Poisson Boltzmann Surface Area (MM-PBSA) method; (d) calculating subtotal binding free energy ($\Delta G_{subtotal\ alanine\ substituted\ variant}$) of an alanine substituted variant of the neuregulin-1β or the fragment thereof with the ErbB3 or the ErbB4 by Molecular Mechanics Poisson Boltzmann Surface Area (MM-PBSA) method, wherein the alanine substituted variant comprises an amino acid of the neuregulin-1β or the fragment thereof substituted by an alanine; (e) calculating $\Delta\Delta G_{subtotal} = \Delta G_{subtotal\ wildtype} - \Delta G_{subtotal\ alanine\ substituted\ variant}$; (f) selecting an alanine substituted variant that has a value of about zero for $\Delta\Delta G_{subtotal}$ for the complex of the neuregulin-1β or the fragment thereof and the ErbB4 and has a negative value for $\Delta\Delta G_{subtotal}$ for the complex of the neuregulin-1β or the fragment thereof and the ErbB3; whereby a polypeptide variant of neuregulin-1β that unchanged binding affinity to ErbB4 but has decreased binding affinity to ErbB3 is identified.

The invention also provides a polypeptide variant of a neuregulin-1β identified by the methods described herein.

D. METHODS OF USING NRG-1β VARIANTS

The invention also provides methods for preventing, treating, or delaying development of diseases in an individual comprising administering to an individual a pharmaceutical composition comprising a polypeptide variant of NRG-1β described herein via activating ErbB2/ErbB3 and/or ErbB2/ErbB4 receptors.

The diseases that can be prevented, treated, or delayed for development include diseases occurring in bone, ear, eye, eye lid, head, neck, heart, throat, lower jaw; mandibular condyle, upper jaw, mouth, nose, nasal pharynx, oral cavity, pancreas, parotid gland, pinna, pituitary gland, prostate, retina, salivary gland, skin, muscle, bone marrow, thyroid gland, tonsil, neuronal system, respiratory system, digestive system, circulatory system, reproductive system, urinary system, endocrine system, cardiovascular system and the hemopoietic system.

As used herein, an "individual" is a mammal, more preferably a human. Mammals include, but are not limited to, farm animals (such as cows, pigs, sheep, goats), sport animals, pets (such as cats, dogs, horses), primates, mice and rats.

In some embodiments, the polypeptide variants of neuregulin-1β used for preventing, treating or delaying development of a disease has an enhanced binding affinity to ErbB2/ErbB3 receptors. In some embodiments, the polypeptide variants of neuregulin-1β comprise the amino acid sequence shown in SEQ ID NO:1, wherein the polypeptide variant comprises a different amino acid than that in SEQ ID NO:1, wherein the polypeptide variant has an enhanced binding affinity to ErbB3 compared to polypeptide of SEQ ID NO:1, and wherein at residue 25 said different amino acid is A, C, E, F, G, H, I, K, L, M, N, P, Q, R, S, T, V, W, or Y; at residue 35 said different amino acid is A, C, D, E, F, G, H, I, L, N, M, P, Q, R, S, T, V, W, or Y; and/or at residue 46 said different amino acid is A, C, D, E, F, G, H, I, K, L, M, N, P, R, S, T, V, W, or Y. In some embodiments, the polypeptide variant of neuregulin-1β consists of amino acid residues 1-52 of SEQ ID NO:1, wherein the polypeptide variant comprises a different amino acid than that in SEQ ID NO:1, wherein the polypeptide variant has an enhanced binding affinity to ErbB3 compared to polypeptide consisting of amino acid residues 1-52 of SEQ ID NO:1, and wherein at residue 25 said different amino acid is A, C, E, F, G5 H, I, K, L, M, N, P, Q, R, S, T, V, W, or Y; at residue 35 said different amino acid is A, C, D, E, F, G, H, I, L, N, M, P, Q, R, S, T, V, W, or Y; or at residue 46 said different amino acid is A, C, D, E, F, G, H, I, K, L, M, N, P, R, S, T, V, W, or Y. In some embodiments of the polypeptide variants, at residue 25 said different amino acid is A; at residue 35 said different amino acid is A; and/or at residue 46 said different amino acid is A.

The diseases that can be prevented, treated, or delayed for development via preferentially activating ErbB2/ErbB3 receptors include nervous system diseases (such as central nervous system, peripheral nervous system), schizophrenia, bone marrow diseases, menix diseases, demyelinate diseases, extrapyramidal system diseases. In some embodiments, the nervous system disease is schizophrenia.

In some embodiments, the polypeptide variants of neuregulin-1β used for preventing, treating or delaying development of a disease has an enhanced binding affinity to ErbB2/ErbB4 receptors. In some embodiments, the polypeptide variant of neuregulin-1β comprises the amino acid sequence shown in SEQ ID NO:1, wherein the polypeptide variant comprises a different amino acid than that in SEQ ID NO:1, wherein the polypeptide variant has an enhanced binding affinity to ErbB4 compared to polypeptide of SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y. In some embodiments, the polypeptide variant of neuregulin-1β consists of amino acid residues 1-52 of SEQ ID NO:1, wherein the polypeptide variant comprises a different amino acid than that in SEQ ID NO:1, wherein the polypeptide variant has an enhanced binding affinity to ErbB4 compared to a polypeptide consisting of amino acid residues 1-52 of SEQ ID NO:1, and wherein at residue 16 said different amino acid is A, C, D, E, F, G, H, I, K, L, M, P, Q, R, S, T, V, W, or Y; at residue 29 said different amino acid is A, C, D, E, F, G, H, I, K, L, M, N, Q, R, S, T, V, W, or Y; at residue 31 said different amino acid is A, C, D, E, F, G, H, I, K, L, M, N, P, Q, S, T, V, W, or Y; at residue 43 said different amino acid is A, C, E, F, G, H, I, K, L, M, N, P, Q, R, S, T, V, W, or Y; and/or at residue 47 said different amino acid is A, C, D, E, F, G, H, I, K, L, M, P, Q, R, S, T, V, W, or Y. In some embodiments of the polypeptide variant, at residue 16 said different amino acid is A; at residue 29 said different amino acid is A; at residue 31 said different amino acid is A; or at residue 47 said different amino acid is A. In some embodiments, the polypeptide variants of neuregulin-1β used for preventing, treating or delaying development of a disease has a binding affinity to ErbB2/ErbB4 receptors similar to the polypeptide of SEQ ID NO:1 or the polypeptide consisting of amino acid residues 1-52 of SEQ ID NO:1, but has decreased binding affinity to ErbB3 than the polypeptide of SEQ ID NO:1 or the polypeptide consisting of amino acid residues 1-52 of SEQ ID NO: 1. In some embodiments, the polypeptide variant comprises the amino acid sequence shown in SEQ ID NO:1, wherein the polypeptide variant comprises a different amino acid than that in SEQ ID NO:1, wherein the polypeptide variant has a decreased binding affinity to ErbB3 compared to the polypeptide of SEQ ID NO:1 but has a binding affinity to ErbB4 similar to the polypeptide of SEQ ID NO:1, and wherein at residue 33 said different amino acid is A.

In some embodiments, the polypeptide variants of neuregulin-1β used for preventing, treating or delaying development of a disease has a decreased binding affinity to ErbB2/ErbB4 receptors. In some embodiments, the polypeptide variant of neuregulin-1β comprises the amino acid sequence shown in SEQ ID NO:1, wherein the polypeptide variants has a decreased binding affinity to ErbB4 compared to polypeptide of SEQ ID NO:1, and wherein at residue 3 said different amino acid is A, C, D, E, F, G, H, I, K, M, N, P, Q, R, S, T, V, W, or Y. In some embodiments, the polypeptide variant of neuregulin-1β consists of amino acid residues 1-52 of SEQ ID NO:1, wherein the polypeptide variant comprises a different amino acid than that in SEQ ID NO:1, wherein the polypeptide variant has an enhanced binding affinity to ErbB4 compared to a polypeptide consisting of amino acid residues 1-52 of SEQ ID NO:1, and wherein at residue 3 said different amino acid is A, C, D, E, F, G, H, I, K, M, N, P, Q, R, S, T, V, W, or Y. In some embodiments of the polypeptide variant, at residue 16 said different amino acid is A.

The diseases that can be prevented, treated, or delayed for development via preferentially activating ErbB2/ErbB4 receptors include, but are not limited to, heart failure, myocardial infarction, dialated cardiomyopathy, and myocarditis (e.g., viral myocarditis), cardiac toxicity.

The formulation, dosage and route of administration of a polypeptide variant of neuregulin-1β described herein, or a nucleic acid encoding the polypeptide variant of neuregulin-1β, preferably in the form of pharmaceutical compositions, can be determined according to the methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of Peptides and Proteins*, Hovgaard and Frkjr (Ed.), Taylor & Francis, Inc., 2000; *Medical Applications of Liposomes*, Lasic and Papahadjopoulos (Ed.), Elsevier Science, 1998; *Textbook of Gene Therapy*, Jain, Hogrefe & Huber Publishers, 1998; *Adenoviruses: Basic Biology to Gene Therapy*, Vol. 15, Seth, Landes Bioscience, 1999; *Biopharmaceutical Drug Design and Development*, Wu-Pong and Rojanasakul (Ed.), Humana Press, 1999; *Therapeutic Angiogenesis: From Basic Science to the Clinic*, Vol. 28, Dole et al. (Ed.), Springer-Verlag New York, 1999). A polypeptide variant of neuregulin-1β described herein, or a nucleic acid encoding a polypeptide variant, can be formulated for oral, rectal, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular polypeptide variant of NRG-1β, or a nucleic acid encoding the polypeptide variant, which is being used.

A polypeptide variant of neuregulin-1β as described herein, or a nucleic acid encoding a polypeptide variant, can be administered alone. Alternatively and preferably, the polypeptide variant of neuregulin-1β, or a nucleic acid encoding the polypeptide variant, is co-administered with a pharmaceutically acceptable carrier or excipient. Any suitable pharmaceutically acceptable carrier or excipient can be used in the present method (See e.g., *Remington: The Science and Practice of Pharmacy*, Alfonso R. Gennaro (Editor) Mack Publishing Company, April 1997).

The nucleic acid encoding a polypeptide variant of NRG-1β can be used in the form of naked DNA, complexed DNA, cDNA, plasmid DNA, RNA or other mixtures thereof as components of the gene delivery system. In another embodiment, the nucleic acid encoding a polypeptide variant of neuregulin-1β, is included in a viral vector. Any viral vectors that are suitable for gene therapy can be used. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and Vaccinia virus vectors can be used. In addition, the genes can be delivered in a non-viral vector system such as a liposome wherein the lipid protects Hie DNA or other biomaterials from oxidation during the coagulation.

According to the present invention, a polypeptide variant of neuregulin-1β described herein, or a nucleic acid encoding a polypeptide variant, alone or in combination with other agents, carriers or excipients, may be formulated for any suitable administration route, such as intracavernous injection, subcutaneous injection, intravenous injection, intramuscular injection, intradermal injection, oral or topical administration. The method may employ formulations for injectable administration in unit dosage form, in ampoules or in multi-dose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in me present invention may employ the use of a foam, gel, cream, ointment, transdermal patch, or paste.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, a polypeptide variant of neuregulin-1β, or a nucleic acid encoding a polypeptide variant, alone or in combination with other agents, may be combined as the active agent in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the polypeptide variant of neuregulin-1β, or a nucleic acid encoding the polypeptide variant, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of a polypeptide variant of neuregulin-1β described herein, or a nucleic acid encoding the polypeptide variant, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

E. EXAMPLES

The following examples are included for illustrative purposes only and are not intended to limit the scope of the invention.

Example 1

Screening for NRG-1β Variants that Selectively Activate a ErbB Receptor

Methods
1. Construction of 3D Models of the Proteins

The x-ray crystal structure of the human EGF and receptor extracellular domains (PDB entry 1IVO) and NMR structure of Neuregulin-alpha (NRG-α) epidermal growth factor (EGF)-like domain (PDB entry 1HAF) were obtained from the Protein Data Bank. The amino acid sequences of ErbB3 (ERB3_HUMAN), ErbB4 (ERB4_HUMAN), and NRG-1β (NRG1-HUMAN) were obtained from the Swiss_Prot/TrEMBL database.

All models were generated using the Homology module of the Insight II software (Accelrys Corporate, San Diego, Calif.). The NMR coordinates of Neuregulin-α were used to model the initial structure of Neuregulin-1β (NRG-1β$_{177-229}$). The pairwise sequence alignments between the target sequences of ErbB3 and ErbB4 and the template EGFR sequence were performed against each of the homology sequences, respectively. The position of the disulphide bonds between the cysteine residues was achieved using the aligned cysteine residues of the target and the corresponding disulphide bridges in the template. Gaps were inserted into the sequences to find an optimal alignment with a length-independent gap penalty of 6. The final sequence alignments of ErbB3 and ErbB4 with EGFR are shown in FIG. 1. Regions of the structural similarity were automatically selected and employed to build a framework for the model structure. Wherever the two aligned residues were the same, the template side-chain geometry was adopted in the target. Otherwise, the side chain in the template was replaced by that of corresponding target residue by aligning the Cα-Cβ bonds. Gap regions were generated by searching for a suitable fragment from protein databank screening and the in-house database. The final loop conformation was chosen from one of the top 10 structures that had the lowest root mean square (RMS) values with compatible geometries between the target and a suitable fragment. Some missing atoms were also added to incomplete side chains of each of these models using the Biopolymer module in Sybyl to ensure proper assignment of hydrogens and atomic charge. The preliminary models were then subject to evaluation by PROCHECK and Profiles-3D to examine the stereo-chemical quality and the protein structure of the models. In the model evaluation by Profiles-3D, a self-compatibility score (S) was determined for each residue in the sequence.

After the initial models of ErbB3, ErbB4 and NRG-1β were built separately, NRG-1β/ErbB3 and NRG-1β/ErbB4 complexes were constituted by superimposing the models with the EGF/EGFR complex. The resulting structures were optimized by energy minimization using the Amber force field implemented in the Sybyl software package. The backbone atoms of all model residues were first fixed during the initial stages of refinement to prevent the backbone from deforming significantly. Then the number of constraints applied to the model was reduced during subsequent cycles. For minimization the following parameters were used: Kollman-united-atom force field and united-atom charge, distant-dependent dielectric constant of 4.0R, 9.5 Å cutoff for non-bonded calculations, and conjugate gradient minimization until the root-mean-square (RMS) gradient in the energy was less than 0.05 kcal/mol·Å. The refined models were then subjected to molecular dynamics simulations.

2. Estimation of Ligand-Binding Contribution by Molecular Dynamics Simulations of NRG1β in Complex with the Receptor Several sets of molecular dynamics (MD) simulations were performed on protein complexes and mutant structures separately using the AMBER 7.0 simulation package and the Parm99 force field. The complex structures were solvated using a box of TIP3P water molecules extending at least 10 Å away from the boundary of any protein atoms. The NRG-1β/ErbB3 structure was solvated in a 100×96×83 Å box of 7976 TIP3P water, and the NRG-1β/ErbB4 structure was solvated in a 104×102×87 Å box of 8075 TIP3P water molecules. An appropriate number of counterions were added to neutralize the system. The Particle Mesh Ewald (PME) method was employed to calculate the long-range electrostatics interactions. All the MD runs were set up using the same protocol. First, the solvent complexes were subjected to 200 steps of minimization using the steepest descent method followed by conjugate gradient to remove close van der Waals contacts. Then, a second minimization of 500 steps was performed on the entire protein-ligand-water complexes.

The relaxed structures were then subjected to MD simulations. Each system was gradually heated from 0 to 300 K in 15 ps with three intervals, and then equilibrated for 25 ps at 300 K, followed by a data collection run, giving a total simulation time of 1100 ps for NRG-1β/ErbB3 and 900 ps for NRG-1β/ErbB4. The non-bonded cutoff was set to 8.0 Å and the nonbonded pairs were updated every 25 steps. The SHAKE method was applied to constrain all covalent bonds involving hydrogen atoms. Each simulation was coupled to a 300K thermal bath at 1.0 atm pressure by applying the algorithm of Berendsen. The temperature and pressure coupling parameters were set as 0.2 ps and 0.05 ps, respectively. An integration time step of the molecular dynamics calculations was 2 fs. In the energy minimizations and molecular dynamics simulations, periodic boundary conditions were applied in all directions. MD simulations were run on an SGI Origin3800 computer at the Shanghai Institute of Materia Medica.

The analyses of the simulations focused on the production stages. The root mean square deviations (RMSDs) of the backbone were calculated from the trajectories at 1 ps intervals, with the initial structure as the reference. The root mean square fluctuation (RMSF) of each residue was calculated similarly. The binding interactions between receptors and ligand were analyzed on the completed models using the program LIGPLOT.

3. Calculation of Free Energy of NRG-1β in Complex with the Receptor by MM-PBSA Method Coordinates from the dynamic trajectory were used every 4 ps (100 snapshots out of 400 ps were processed), and the MM-PBSA calculation was performed on each of them using the AMBER 7.0 program. For each snapshot collected during the simulation, the ligand-protein binding free energy ($\Delta G_{binding}$) was calculated using Eq. (1):

$$\Delta G_{binding} = \Delta G_{Complex} - [\Delta G_{protein} + \Delta G_{ligand}] \quad (1)$$

where $\Delta G_{complex}$, $\Delta G_{protein}$ and $\Delta G_{ligand}$ are the free energies of the complex, protein and ligand. Each free energy term in Eq. (1) was calculated with the absolute free energy of the species (protein, ligand and their complex) in gas phase ($E_{gas}$), the solvation free energy ($\Delta G_{solvation}$) and the entropy term (T$\Delta$S) using Eq. (2):

$$\Delta G = E_{gas} + \Delta G_{solvation} - T\Delta S \quad (2)$$

$E_{gas}$ is the sum of the internal strain energy ($E_{int}$), van der Waals energy ($E_{vdw}$) and electrostatic energy ($E_{electrostatic}$) (Eq. (3)). $E_{int}$ is the energy associated with vibrations of covalent bonds and bond angles, rotation of single bond torsional angles (Eq. (4)).

$$E_{gas} = E_{int} + E_{vdw} + E_{electrostatic} \quad (3)$$

$$E_{int} = E_{bond} + E_{angle} + E_{torsion} \quad (4)$$

The solvation free energy, $\Delta G_{solvation}$, is approximated as the sum of the polar contribution ($G_{PB}$) and nonpolar contribution ($G_{nonpolar}$) using a continuum representation of the solvent:

$$\Delta G_{solvation} = G_{PB} + G_{nonpolar} \quad (5)$$

The polar contribution ($G_{PB}$) to the solvation energy was calculated using the DELPHI program with PARSE atom radii and standard Parm94 charges for amino acids. The grid size used was 0.5 Å. The dielectric constant was set to 1 for interior solute and 80 for exterior water. A total of 1000 iterations were performed for each $G_{PB}$ calculation to achieve a better convergence. The nonpolar contributions ($G_{nonpolar}$) were estimated using a simple equation: $G_{nonpolar} = \gamma \times$ SASA+b kcal/mol. SASA is the solvent-accessible surface area that was estimated using the MSMS algorithm with probe radius of 1.4 Å. The surface tension proportionality constant γ and the free energy of nonpolar salvation for a point solute b were set to 0.00542 kcal mol$^{-1}$ Å$^{-2}$ and 0.092 kcal mol$^{-1}$, respectively.

The entropy calculation is extremely time-consuming for large systems. In this study, only $\Delta G_{subbtotal}$ (without term of –T$\Delta$S) was estimated to address the mutation effect to the binding free energy.

4. Analysis of Computational Alanine-Scanning Mutagenesis

The computational alanine-scanning method was applied to estimate the relative binding affinity of different NRG-1β variants to ErbB3 and ErbB4, respectively. Two methods were used to calculate the relative binding strength of different peptide mutants. In the first approach, the structures of complex, protein and peptide were taken from the same snapshot of the complex trajectories. The alanine mutant structures were generated by altering the coordinates of the wild-type trajectory. This method involved deleting atoms and truncating the mutated residue at Cγ by replacing with a hydrogen atom. All parameters in the topology files for the mutated residues were accordingly replaced with the alanine residue parameters. A total of 100 snapshots out of 400 ps (every fourth snapshot) were obtained for energy calculation. The relative binding free energy is the free energy difference between the wild-type and alanine mutated.

In the second method for calculating the relative binding free energy, we conducted several sets of separate dynamics simulations for the alanine mutated NRG-1β peptides in the complexes with ErbB3 and ErbB4, respectively. Then the energy components were calculated from 100 snapshots out of 400 ps collected trajectories (every fourth snapshot) and statistical analyses were carried out.

Results

1. Modeling Results and Evaluation

The 3D models of ErbB3 and ErbB4 were constructed by homology modeling based on the x-ray crystal structure of the complex formed between human epidermal growth factor (EGF) and the extracellular domain of the EGF receptor (EGFR). FASTA and BLAST searches of sequence databases produced several structures that are homologous to ErbB3 and ErbB4. Within the EGFR family, we found that the x-ray structures of unliganded ErbB3 (PDB entry 1M6B), inactivated EGFR in complex with EGF (PDB entry INQ1), ErbB2 bounded by Herceptin Fab (PDB entry 1N8Z) and the complex of EGF/EGFR (PDB entry 1IVO) were among the homologous proteins with higher sequence identities to ErbB3 and ErbB4. ErbB2 is an unusual receptor of the EGFR family for which no high-affinity ligand has been found. The unliganded ErbB3 has an identical sequence compared with the receptor of NRG-1β/ErbB3 complex. To focus on ligand/receptor interactions, the structure of the EGF/EGFR complex was selected as the template for structural modeling.

On the basis of internal sequence conservation and identity among the EGF receptor family members, the extracellular domain has been classified into four domains (I to IV). Domains II and IV are richer in cysteine residues, containing 24 and 21 cysteines, respectively. In the crystal structure of EGFR, most of domain IV (residues 513 to 619) is structurally disordered. Therefore, the region of domain IV was excluded in our homology modeling. The sequences of ErbB3 (residues 8-511) and ErbB4 (residues 25-533) have 44% and 48% identity with EGFR (residues 3-512). Furthermore, another 40% of these residues were conservative substitutions, giving an overall sequence similarity of about 80% for both ErbB3 and ErbB4 to EGFR as shown in FIG. 1.

The accuracy of a model can vary significantly even within different regions of the same protein: usually highly-conserved regions can be modeled much more reliable than the variable loops or surface residues. A total of 7 and 4 structurally conserved regions (SCRs) were deduced for ErbB3 and ErbB4 respectively, which constituted major segments of the total sequences (FIG. 1). Coordinates for the remaining parts of the sequence, designated structurally variable regions (SVRs), were generated by searching a protein structure database as described above in the Methods. FIG. 2 shows stereo plots of the two refined models superimposed with the x-ray structure of EGFR. It is clear that the overall topology of the template protein has been inherited while some significant local conformation changes are presented in the variable regions. The Cα backbone root mean square deviations (RMSDs) of the refined models from their template are small, 0.55 Å for ErbB3 and 0.39 Å for ErbB4, indicating a high degree of structural similarity, as expected from their high degree of sequence homology.

Several key residues of this receptor family such as Leu69, Leu98, Val350, Asp355 and Phe357 in EGFR which interact hydrophobically with residues of EGF are conserved in ErbB3 and ErbB4 as well. EGFR has a stack of glycine residues at positions 39, 63, 85, and 122 in domain 1 and 343, 379, 404, and 435 in domain III. These residues are conservatively retained in corresponding conformations in the ErbB3 and ErbB4 models. Like EGFR, both domains I and III of ErbB3 and ErbB4 comprise six turns of a β-helix capped at each end by a helix and a disulfide bond. In domains I and III of ErbB3 and ErbB4, there are also conserved tryptophans (Trp176, Trp492 for ErbB3 and Trp198, Trp513 for ErbB4) inserted between the fourth and fifth turns of the β-helix. Domain II of the receptors has a similar fold to the second domain of EGFR, which is composed of several small modules with similar disulphide-bond connectivities.

The models were then evaluated by a Ramachandran plot structure validation test using PROCHECK. The Ramachandran plot analyzes the backbone phi (ϕ), psi (ψ) torsional angles of a protein and calculates the percentage occupancies for "favoured" "allowed", "generously allowed," and "disallowed" regions as a quality measurement of a protein structure. The values obtained for the models of ErbB3 and ErbB4 are summarized in Table 1 below. Altogether 96.2% and 97.5% of the residues were in favoured and allowed regions for the models of ErbB3 and ErbB4, respectively. In addition to the evaluation of stereochemical quality for the models, we also performed Profiles-3D analyses to further evaluate the models by checking the quality of side-chain packing. The overall quality scores for ErbB3 and ErbB4 are 230.51/257.48 and 216/256.56 respectively, where the denominator denotes the expected score for a protein of this length based on known structures. For comparison, scores of 115.87/257.48 and 115.45/256.56 or less, would suggest the structure is almost certainly incorrect. After successful validation, the quality of ErbB3 and ErbB4 structures appear to be acceptable for further study.

TABLE 1

Ramachandran plot calculations on 3D models of ErbB3 and ErbB4 computed with the PROCHECK program.

|  | ErbB3 | ErbB4 |
| --- | --- | --- |
| % of residues in most favoured regions | 68.0 | 73.9 |
| % of residues in additional allowed zones | 28.2 | 23.6 |
| % of residues in generously allowed regions | 2.3 | 0.8 |
| % of residues in disallowed regions | 1.5 | 1.6 |
| % of non-glycine and non-proline residues | 100.0 | 100.0 |

A homology model for NRG-1β$_{(177-229)}$ was constructed from the NRG-α structure (PDB entry 1HAF) with an overall sequence identity of 80%. For convenience, we chose to number the residues in this NRG-α domain sequentially from 1 to 63. The C-terminal residues 51 to 63 are disordered and flexible in the solution structure of NRG-α. The more ordered region (residues 1-50) has been shown to be the minimal subunit required for binding to cellular receptors. Thus, a truncated model of NRG-1β, consisting of residues 1-52, was built as described in the method. The model includes an N-terminal subdomain containing a central three-stranded β-sheet, a helical region, and a short β-sheet in the C-terminal subdomain. NRG-1β is stabilized by three disulfide bridges, Cys6-Cys20, Cys14-Cys34 and Cys36-Cys45.

2. Modeling of NRG-1β Binding to Receptors

Figure 3:
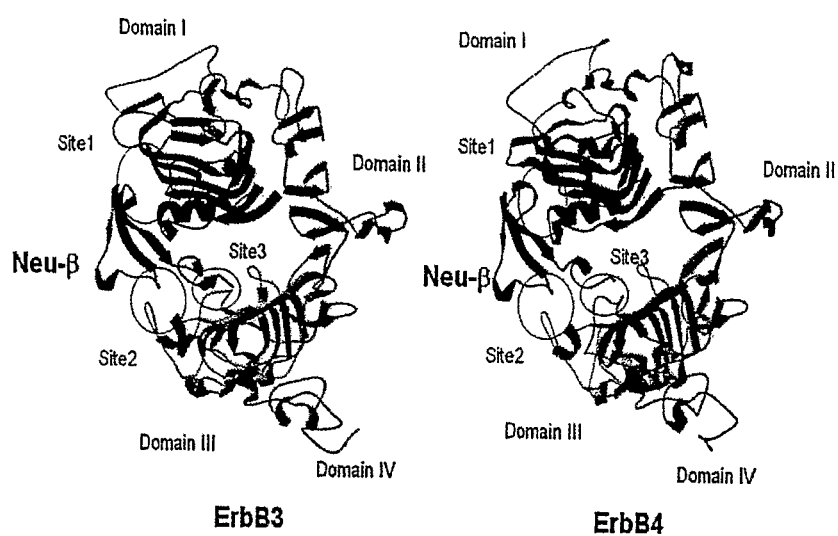
FIG. 3 shows ribbon diagrams of (A) NRG-1β/ErbB3 and (B) NRG-1β/ErbB4 (B) models. NRG-1β chain in complex is red. Domains I, II, III, and IV in the receptor are colored blue, green, orange and gray, respectively. Three binding sites in the interface are outlined. The figures were produced using the program MOLSCRIPT.

The final 3D models of the NRG-1β/ErbB3 and NRG-1/ErbB4 complexes are shown in FIG. 3. In each complex, domains I, II and III of the receptors are arranged in a C shape, and NRG-1β is accommodated between domains I and III in a similar way of EGF binding to EGFR (FIG. 3). This is consistent with the previous biochemical results that domains I and III of ErbB3 may be involved in the NRG-1β binding. The binding affinity studies suggest that the binding determinants on the ErbB3 and ErbB4 receptors are very similar although they have substantial overall sequence diversity. Mutagenesis studies also revealed that both the N- and C-termini of NRG-1β are important for ligand-receptor binding. These two regions are far away in distance from each other in the folded protein, supporting the role of multiple regions of ligand-receptor interaction. The intervening residues, in particular those that are conserved between NRG-1β and EGF, may play purely structural roles by maintaining the appropriate distance and orientation between these two regions. The X-ray structure of the unliganded ErbB3 shows that the size of the ligand binding site between domains I and III is twice as big as the ligand size when domains II and IV interact. The domain II and IV contact seems to constrain the relative orientations of domains I and III for ligand binding. Thus, a ligand that contacts only to domain I (or domain III) would bind the receptor but fail to induce the domain arrangement that seems necessary for signaling. Based on these results, we can conclude that there are at least two receptor binding sites required for signal required of transduction.

Comparison of the NRG-1β structure with EGF revealed a high degree of structural similarity (FIG. 4). Excluding the N-terminal region (Ser1-Lys5), the disordered Ω-loop (Lys24-Ser30) and C-terminal region (Met50-Ser52), the $C_\alpha$ atoms of NRG-1β aligns well with that of EGF, with an RMSD of ~1.3 Å. NRG-1β has a three-residue insertion relative to the sequence of EGF. However, the substitution of residues 21-33 in the NRG-1β with residues 21-30 of EGF has no effect on neuregulin receptor binding or its ability to stimulate receptor phosphorylation. The experimental results suggested that the functional significance of the three-residue (residues 28-30) insertion in the NRG-1β is minimal, despite the significant structural differences in that region. Therefore, the orientation of the extended loop in NRG-1β would not affect the modeling of NRG-1β binding to the receptors.

3. Molecular Dynamics Simulations

The behavior of the receptor-ligand complexes was studied by molecular dynamics simulations to account for protein flexibility and conformational changes. The starting models of NRG-1β/ErbB3 and NRG-1β/ErbB4 were subjected to 1.1 ns and 0.9 ns of MD simulations, respectively. The root mean square deviations (RMSDs) of $C_\alpha$ atoms from their initial positions (t=0 ps) have been used to measure the stability and to gain insight into possible structure fluctuation.

Figures 4B, 5:
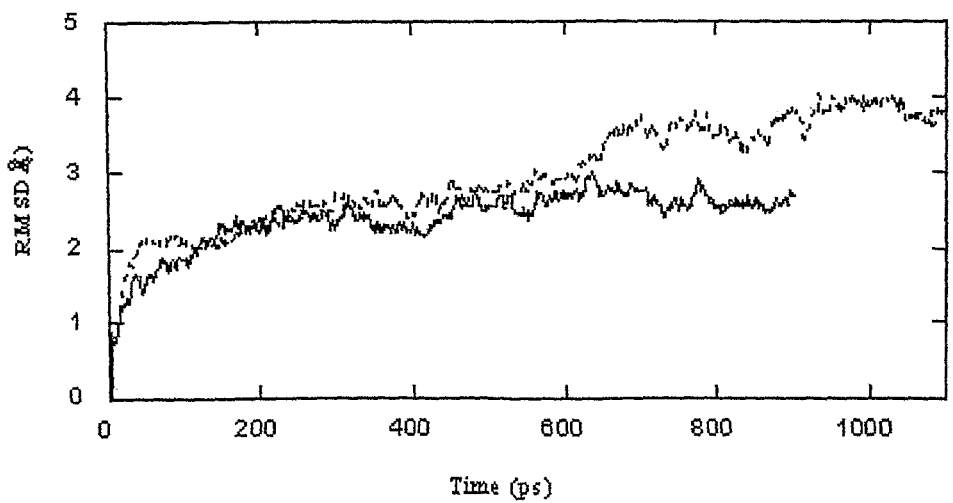

The time evolution of the $C_\alpha$ atom RMSDs of NRG-1β/ErbB3 and NRG-1β/ErbB4 complexes is presented in FIG. 5. In the plot, a sharp rise was observed during the first 100 ps in all residue RMSDs and then it tends to flatten out. The magnitude of these RMSD curves, however, did not continue to increase during the data collection period, implying that the structures of NRG-1β/ErbB3 and NRG-1β/ErbB4 were stable over this time scale. The average RMSDs was below 3.0 Å over the entire simulation for both NRG-1β/ErbB3 and NRG-1β/ErbB4 complexes. Particularly, the simulation trajectories of the ErbB4 with ligand NRG-1β appeared to be well equilibrated with an average RMSD value of 2.6 Å over the last 400 ps. The NRG-1β bound ErbB3 structure showed a higher RMSD with average value of 3.7 Å during the last 400 ps simulation. This is indicative of the relative stability of the NRG-1β bounded structures. This trend was again apparent in the analysis of residue-wise RMS fluctuations. The residues of ErbB3 in the NRG-1β bound structure fluctuate more about their mean positions than the residues in the ErbB4 complex.

Superimposition of the average structures of all trajectories with their respective starting structures revealed regions of major conformational change. Residues that showed the largest deviations in NRG-1β/ErbB3 structure (residues 243-256) are the same as that in the NRG-1β/ErbB4 complex (residues 265-278), but to a great extent. These residues are a part of β-hairpin loop that extends nearly 20 Å from domain II in the x-ray structure of ErbB3. This β-hairpin loop is highly conserved within the EGFR family and plays a dominant role not only in intramolecular contact between domains II and IV but also in intermolecular receptor-receptor interaction. Our 1:1 truncated complex models which lack of interactions between domains II and IV as well as receptor-receptor contacts may result in considerably high RMSDs at this region. But overall analyses show that the modeled structures remain stable along the simulations without suffering remarkable structural changes.

4. Ligand-Receptors Interactions

The ligand-receptor interaction on each receptor consists of three sites as in the interaction in EGF/EGFR, which is designated hereafter as site 1 in domain I and sites 2 and 3 in domain III of the receptor (FIG. 3). Residues 20-35 and Leu3 of NRG-1β interact with site 1. The region containing residues 10-19 and Arg44 of NRG-1β interacts with site 2. The C-terminal region around residue Tyr48 interacts with site 3. These residues of ligand form a variety of electrostatic, hydrophobic, and hydrogen-bonding interactions to the receptor.

From the analysis of hydrogen bond trajectories between the ligand and the receptor, a few key interactions mediated by hydrogen bonds between side chain residues of NRG-1β/ErbB3 and NRG-1β/ErbB4 have been detected. These hydrogen bonds are listed along with distances in Table 2. From this Table 2, it can be seen that the crucial interactions including those of residues Arg44 and Tyr48 in NRG-1β (Arg41 and Arg45 in EGF) with the receptors are retained. The Arg44 side chain of NRG-1β makes a hydrogen bond with the Asp352 side chain of ErbB3 and the Asp376 side chain of ErbB4, respectively. This result is supported by the experimental finding that the replacement of Arg44 by alanine significantly reduced the ErbB3 and ErbB4 binding activity of NRG-1β.

TABLE 2

Hydrogen bonds between residue side chains of ligand and receptor.
Hydrogen bond partners

| NRG-1β | | | | |
|---|---|---|---|---|
| Residue | Group | Residue | Group | Distance (Å) |
| ErbB3 | | | | |
| Asn47 | ND2 | Tyr405 | OH | 2.93 |
| Tyr48 | OH | Asn379 | ND2 | 3.12 |
| Tyr48 | OH | Asn379 | OD1 | 3.10 |
| Arg44 | NH2 | Asp352 | OD2 | 2.61 |
| Arg44 | NH1 | Asp352 | OD1 | 2.67 |
| Asn47 | ND2 | Asp343 | OD1 | 2.90 |
| Arg31 | NH2 | Glu131 | OE2 | 2.75 |
| Arg31 | NH1 | Glu131 | OE1 | 2.92 |
| Asn38 | ND2 | Asn25 | OD1 | 3.25 |
| ErbB4 | | | | |
| Glu39 | OE2 | Lys438 | NZ | 2.87 |
| Tyr48 | OH | Asn403 | OD1 | 2.73 |
| Arg44 | NH2 | Asp376 | OD1 | 3.04 |
| Arg44 | NH1 | Asp376 | OD1 | 3.12 |
| Ser27 | OG | Asp 150 | OD1 | 3.59 |
| Asn28 | ND2 | Tyr148 | OH | 3.16 |
| Lys35 | NZ | Ser40 | OG | 2.82 |
| Asp43 | OD2 | Lys35 | NZ | 2.81 |

Besides the hydrogen bonds, the hydrophobic interactions between NRG-1β and the interfaces of sites 1, 2 and 3 of ErbB3 and ErbB4 are extensive.

Figure 6A:
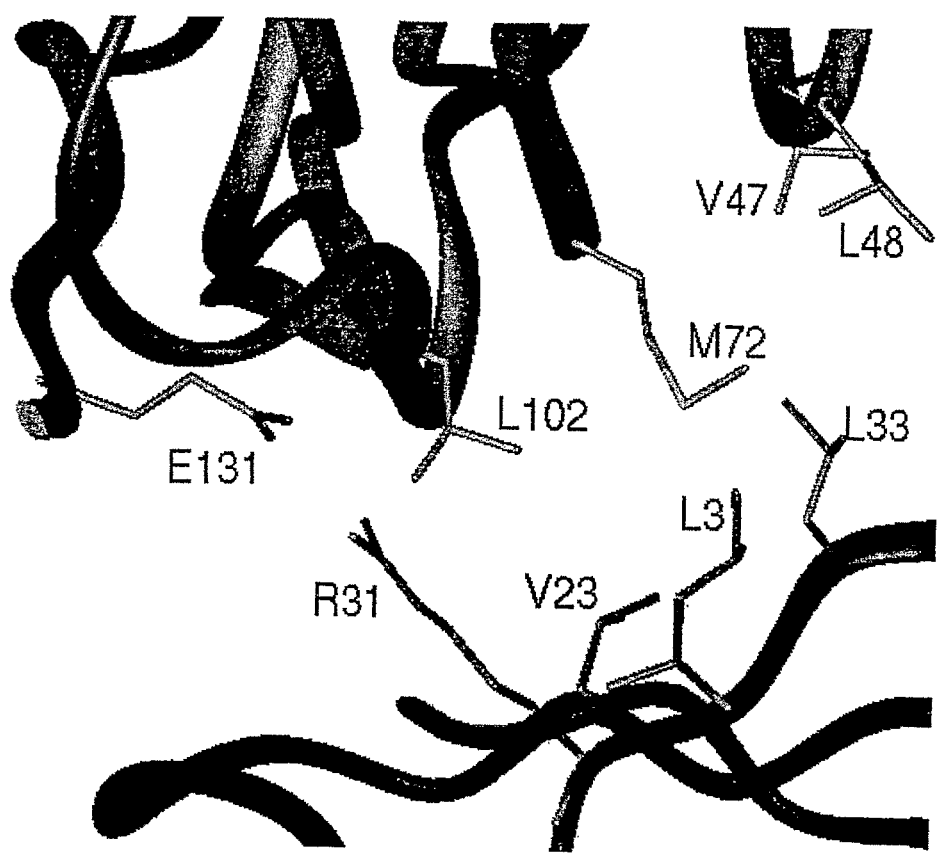
FIGS. 6A-6C show the interactions between ErbB3 and NRG-1β on the three binding sites, (FIG. 6A) the interface at site 1.
Figure 6B:
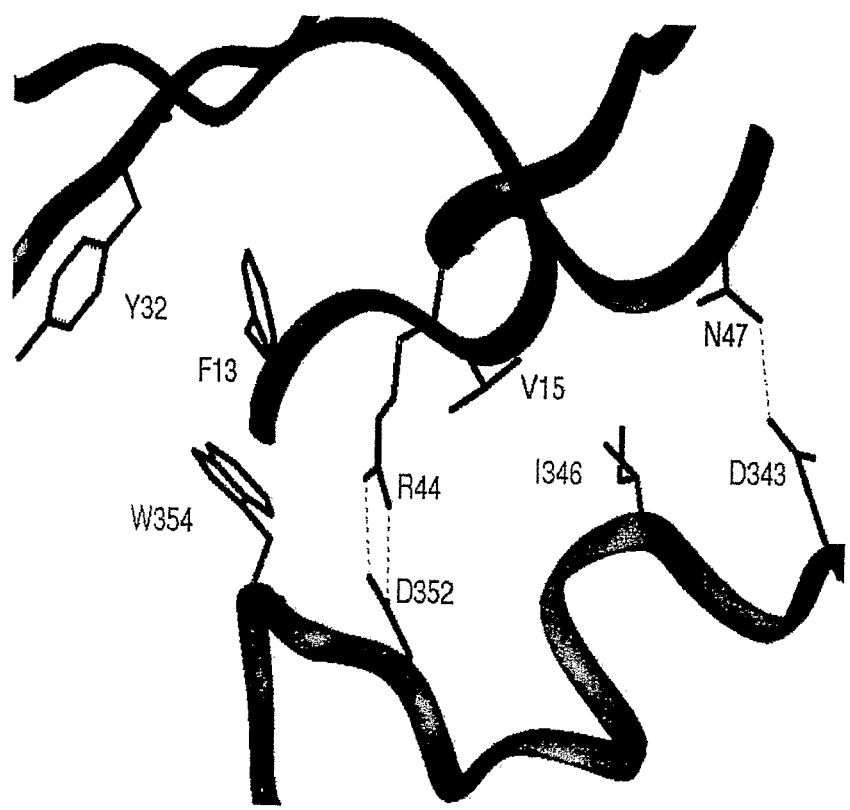

In NRG-1β/ErbB3 complex, the side chains of Val47, Leu48, Met72, and Leu102 in site 1 of ErbB3 hydrophobically interact with Leu3, Val23 and Leu33 of NRG-1β (FIG. 6A). The Trp354 side chain in site 2 of ErbB3 hydrophobically interacts with Phe13 and Tyr32 of NRG-1β (FIG. 6B).

Figure 6C:
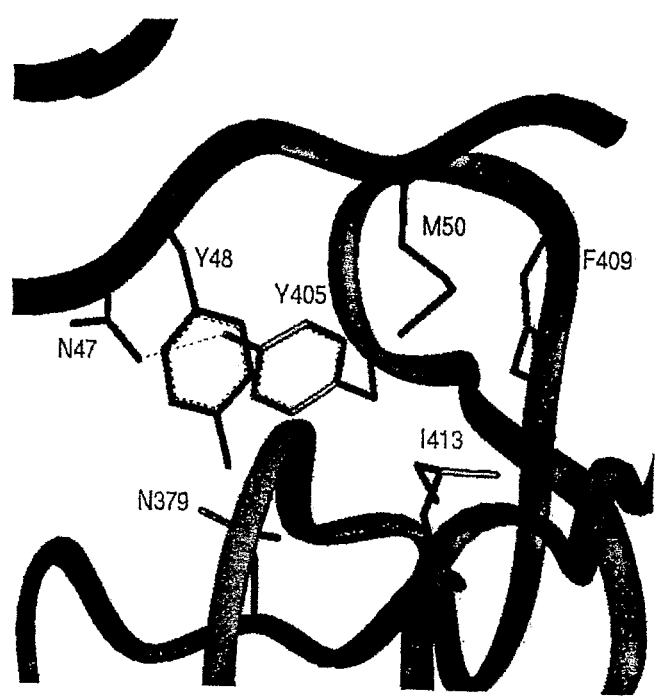

Furthermore, the long aliphatic portion of the Arg44 (NRG-1β) side chain also provides van der Waals contacts with the Trp354 (ErbB3) side chain. The side chains of Tyr405, Phe409 and Ile413 in site 3 of ErbB3 form a hydrophobic interaction network with that of residues around Tyr48 of NRG-1β (FIG. 6C).

Figure 7A:
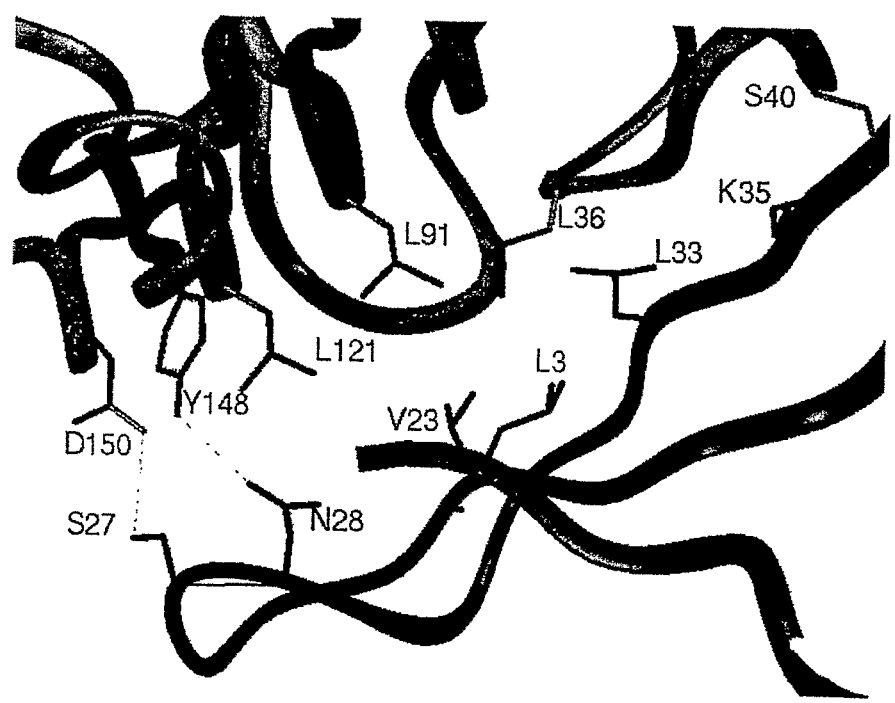
FIGS. 7A-7C show the interactions between ErbB4 and NRG-1β on the three binding sites, (FIG. 7A) the interface at site 1.
Figure 7B:
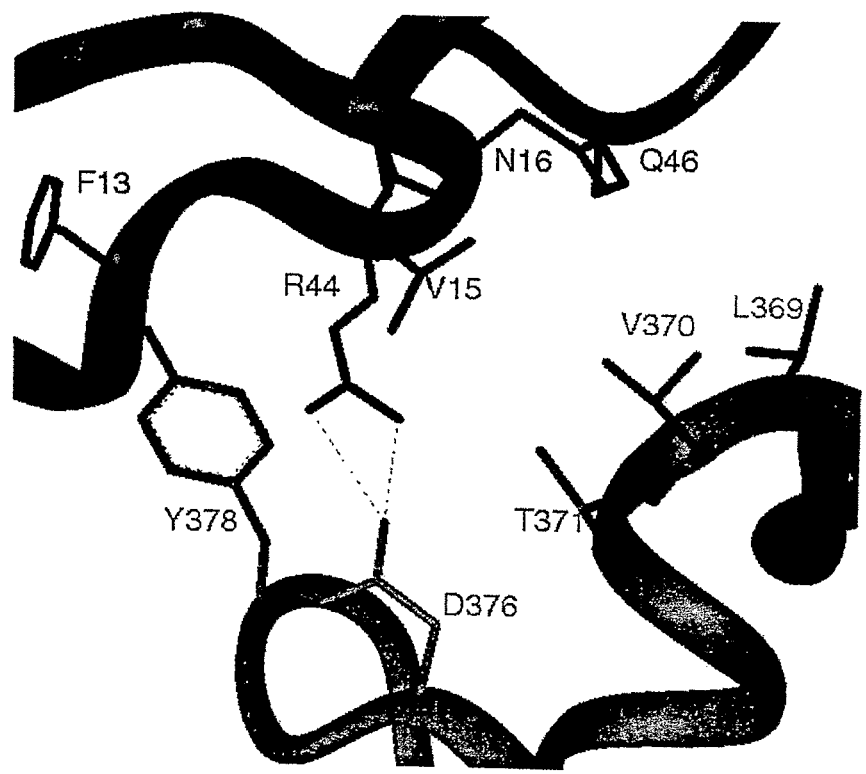
Figure 7C:
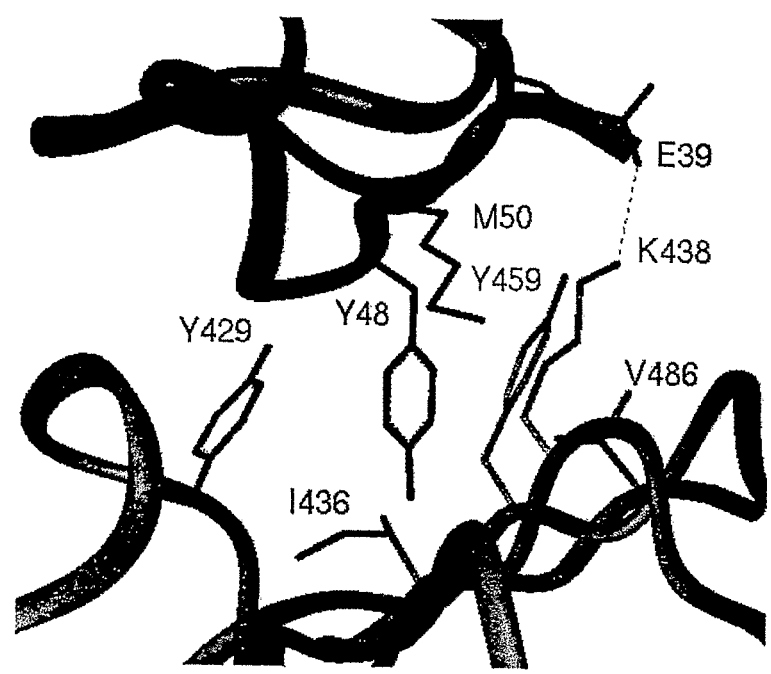

Similar hydrophobic interactions are observed in the NRG-1β/ErbB4 complex. As a result of these interactions, three hydrophobic interaction networks are formed on the interfaces between NRG-1β and ErbB4. The side chains of Leu3, Val23 and Leu33 of NRG-1β form van der Waals contacts with Leu36, Leu91 and Leu121 in site 1 of ErbB4 (FIG. 7A). The side chains of Phe13, Val15 and residues around Tyr48 of NRG-1β have similar interactions with sites 2 and 3 of ErbB4 (FIGS. 7B and 7C), respectively. Both putative interactions identified from refined models are in agreement with the mutagenesis studies of NRG-1β in the presence of ErbB3 or ErbB4.

The binding analysis of NRG-1β with receptors presented above provides us with rich information about the mechanism by which ErbB3 and ErbB4 interacts with NRG-1β. This in turn facilitates our ability to understand and further optimize the interaction components for NRG-1β binding and stability to the receptor by computational mutagenesis approach.

5. Computational Alanine-Scanning Mutagenesis of NRG-1β by MM-PBSA Method

To determine the contribution of each residue in the interaction interface to the ligand-receptor binding and to identify key residues in the ligand that could potentially increase its binding affinity upon mutation, computational alanine-scanning mutagenesis was performed on NRG-1β, and the binding free energies of the mutated ligands to the receptors were calculated using the MM-PBSA method. To reduce computational time, the entropy contribution (T$\Delta$S) to the binding free energy was not calculated in this study. The entropy contributions are expected to be canceled when the differences in the binding free energies are calculated between the wild type and mutants. This assumption seems reasonable, as demonstrated by Massova and Kollman's calculation of T$\Delta$S for a 12-residue peptide derived from human p53 and its mutants. Therefore, only $\Delta G_{subtotal}$ (without the $-T\Delta S$ term) was used as the criteria for the $\Delta G_{binding}$ estimates.

Table 3 shows all the energy terms and the subtotal binding free energies of NRG-1β and its mutants to ErbB3 and ErbB4, respectively. As seen in Table 3, the intermolecular van der Waals interaction and the nonpolar solvation term provide the driving force for the binding. Both complex formations lead to strongly favorable electrostatic interactions ($E_{ele}$), opposed by unfavorable contributions due to the polar part of solvation free energy ($G_{PB}$). Similar results can be found in several other studies. The total electrostatic contributions ($E_{ele}+G_{PB}$) for NRG-1β/ErbB3 and NRG-1β/ErbB4 are 110.2 kcal mol$^{-1}$ and 112.5 kcal mol$^{-1}$, respectively, and thus disfavor complex formation, again in agreement with related studies cited above.

TABLE 3

Results of free energy calculation of NRG-1β with ErbB receptors by MM-PBSA[a]

| Contribution | NRG-1β/ErbB3 | | ErbB3 | | NRG-1β | | Delta[b] | |
|---|---|---|---|---|---|---|---|---|
| Std[d] | Mean[c] | Std[d] | Mean[c] | Std[d] | Mean[c] | Std[d] | Mean[c] | Std[d] |
| $E_{ele}$ | −16753.91 | 112.64 | −14940.46 | 102.75 | −1361.15 | 22.58 | −452.30 | 25.80 |
| $E_{vdw}$ | −2006.94 | 32.49 | −1739.60 | 31.19 | −123.33 | 10.46 | −144.02 | 7.29 |
| $E_{int}$ | 10831.80 | 63.57 | 9798.05 | 60.27 | 1033.75 | 20.77 | 0.00 | 0.00 |
| $E_{gas}$ | −7929.04 | 133.98 | −6882.00 | 123.65 | −450.73 | 25.50 | −596.31 | 25.25 |
| $G_{nonpolar}$ | 143.01 | 1.19 | 132.17 | 1.01 | 19.13 | 0.18 | −8.28 | 0.44 |
| $G_{PB}$ | −7440.22 | 101.09 | −6863.61 | 88.32 | −1139.12 | 18.86 | 562.52 | 25.27 |
| $G_{sol}$ | −7297.21 | 100.53 | −6731.44 | 87.93 | −1120.00 | 18.84 | 554.23 | 25.12 |
| $G_{subtotal}$ | −15226.25 | 66.86 | −13613.45 | 65.36 | −1570.72 | 18.19 | −42.08 | 7.21 |
| -T$\Delta$S | ND | ND | ND | ND | ND | ND | ND | ND |

| Contribution | NRG-1β/ErbB4 | | ErbB3 | | NRG-1β | | Delta[b] | |
|---|---|---|---|---|---|---|---|---|
| Std[d] | Mean[c] | Std[d] | Mean[c] | Std[d] | Mean[c] | Std[d] | Mean[c] | Std[d] |
| $E_{ele}$ | −16888.05 | 94.37 | −15171.74 | 66.74 | −1343.04 | 33.13 | −373.27 | 27.41 |
| $E_{vdw}$ | −2068.19 | 31.77 | −1815.76 | 29.10 | −119.74 | 10.70 | −132.69 | 6.88 |
| $E_{int}$ | 10794.92 | 61.48 | 9749.46 | 56.82 | 1045.46 | 19.44 | 0.00 | 0.00 |
| $E_{gas}$ | −8161.32 | 117.81 | −7238.04 | 90.27 | −417.32 | 43.40 | −505.97 | 26.96 |
| $G_{nonpolar}$ | 138.41 | 1.45 | 126.65 | 1.24 | 19.44 | 0.41 | −7.68 | 0.52 |
| $G_{PB}$ | −7327.22 | 94.47 | −6658.67 | 67.14 | −1153.33 | 36.53 | 485.77 | 25.23 |
| $G_{sol}$ | −7188.82 | 93.77 | −6532.02 | 66.67 | −1134.89 | 36.22 | 478.09 | 25.09 |
| $G_{subtotal}$ | −15359.14 | 68.76 | −13770.06 | 63.84 | −1552.20 | 20.79 | −27.88 | 10.09 |
| -T$\Delta$S | ND | ND | ND | ND | ND | ND | ND | ND |

[a]All value are given in kcal mol$^{-1}$.
[b]Contribution (Complex)-Contribution (Receptor)-Contribution (ligand)
[c]Average over 400 snapshots.
[d]Standard error of mean values.

Based on molecular dynamics simulations of ligand-receptor interactions, we have identified key residues of NRG-1β responsible for binding to receptor residues. Table 4 shows the results of the computational alanine-scanning mutagenesis approach for 20 residues of the total 52 residues of NRG-1β which contribute to the ErbB3 and ErbB4 binding. The positive and negative values of $\Delta\Delta G_{subtotal}$ ($\Delta G_{wildtype}-\Delta G_{mutant}$) indicate favorable and unfavorable substitutions, respectively. Data are also depicted as a graph in FIG. 8. The results in FIG. 8 show that several alanine mutants of NRG-1β have significantly reduced ligand interaction energies with ErbB3 and ErbB4, especially at positions 44, 48 and 50. This can be explained structurally. Residues Arg44 and Tyr48 form hydrogen bonds with polar residues of the receptors (see FIGS. 6 and 7), which are reflected by the major contribution of electrostatic interactions to the binding free energy ($\Delta\Delta E_{ele}$ term; see supplementary Tables 1 and 2). Arg44Ala and Tyr48Ala mutations abolish the important hydrogen bonds between the ligand and receptors. Tyr48Ala and Met50Ala mutations cause significant loss of favorable van der Waals interactions between the ligand and receptors ($\Delta\Delta E_{vdw}$ term; see supplementary Tables 1 and 2).

TABLE 4

Computational alanine-scanning mutagenesis results for NRG-1β complex with ErbB3 and ErbB4 ($\Delta\Delta G_{subtotal} = \Delta G_{wildtype} - \Delta G_{mutant}$)

| NRG-1β Position | NRG-1β/ErbB3 $\Delta\Delta G_{subtotal}$ (kcal/mol) | NRG-1β/ErbB4 $\Delta\Delta G_{subtotal}$ (kcal/mol) |
|---|---|---|
| His2Ala | −0.10 ± 0.54 | 0.13 ± 1.90 |
| Leu3Ala | −1.14 ± 1.24 | −0.87 ± 1.19 |
| Phe13Ala | −1.06 ± 0.76 | −0.25 ± 0.90 |
| Val15Ala | −0.78 ± 0.86 | −1.19 ± 0.63 |
| Asn16Ala | 0.78 ± 0.85 | 1.90 ± 2.94 |
| Val23Ala | −0.50 ± 1.60 | −1.53 ± 1.00 |
| Asp25Ala | 2.26 ± 0.66 | −2.20 ± 3.71 |
| Arg31Ala | −5.90 ± 1.14 | 1.83 ± 4.21 |
| Tyr32Ala | 0.32 ± 0.57 | −0.34 ± 0.01 |
| Leu33Ala | −3.31 ± 0.38 | −0.32 ± 1.27 |
| Lys35Ala | 1.13 ± 0.93 | 0.00 ± 2.09 |
| Asn38Ala | 0.59 ± 0.76 | 1.31 ± 0.89 |
| Glu39Ala | 0.75 ± 2.09 | −0.51 ± 2.67 |
| Phe40Ala | 1.59 ± 2.12 | 1.08 ± 3.50 |
| Arg44Ala | −5.43 ± 4.79 | −5.30 ± 2.77 |
| Gln46Ala | 3.57 ± 2.69 | −1.01 ± 1.62 |
| Asn47Ala | −0.07 ± 2.22 | 2.03 ± 1.72 |
| Tyr48Ala | −2.99 ± 2.45 | −3.05 ± 2.40 |
| Met50Ala | −3.45 ± 0.54 | −1.92 ± 1.45 |
| Ser52Ala | −0.21 ± 1.77 | 0.49 ± 2.25 |

Figure 8A:
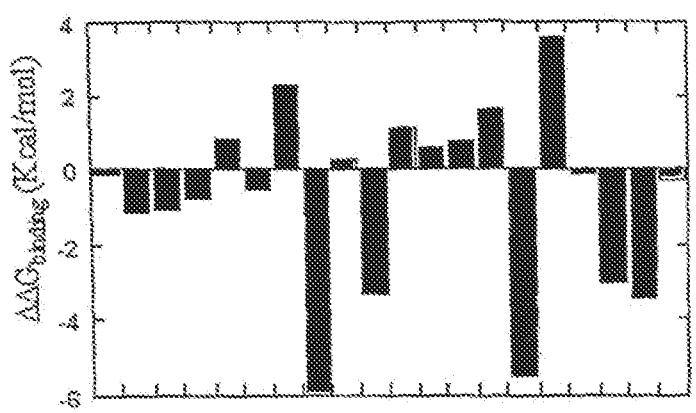
FIGS. 8A and 8B show (FIG. 8A) the binding energy change for the computational alanine scanning mutagenesis experiments for ErbB3 complex with NRG-1β.
Figure 8B:
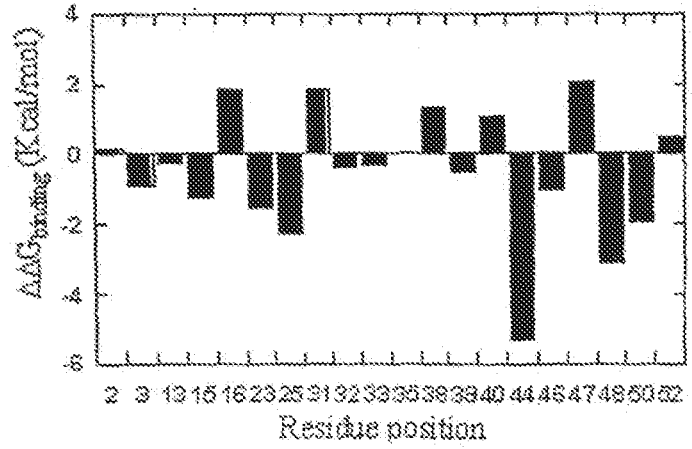

To gain further insight into the contributions of each alanine mutation, the change of the intermolecular van der Waals and electrostatic interactions plus the polar solvation free energies upon alanine mutation is shown in FIG. 8. In most cases the change of intermolecular electrostatic energies is anticorrelated with the change of polar solvation free energies. Therefore, it is important to combine $\Delta\Delta E_{ele}$ and $\Delta\Delta G_{PB}$ together based on the common electrostatic origin of die contributions. From FIG. 8, the $\Delta\Delta G_{nonpolar}$ is very small compared to changes in other free energy components. The contributions of the $\Delta\Delta E_{vdw}$ are mostly negative, which indicate that alanine substitution reduces van der Waals contacts on the binding interfaces. On the other hand, the terms which are the combined of $\Delta\Delta E_{ele}$ and $\Delta\Delta G_{PB}$ are most favored by Ala mutations. One exception is the substitution of Arg44, which loses both van der Waals and electrostatic ($\Delta\Delta E_{ele}$+$\Delta\Delta G_{PB}$) interactions. The intermolecular interactions between the positively-charged Arg44 of NRG-1β and negatively-charged Asp352 of ErbB3 and Asp376 of ErbB4 are strongly favored in the wild type complexes. A similar result is observed for the Arg31Ala substitution of NRG-1β interacting with ErbB3 (FIG. 8A), but not with ErbB4 (FIG. 8B). The structure of NRG-1β/ErbB3 reveals that the Arg31 side-chain forms two hydrogen bonds to the Glu131 side chain of ErbB3 (Table 2). Therefore, Arg31Ala mutant lacks the hydrogen bonding interaction. However, Arg31 of NRG-1β is not involved in hydrogen bonding to the receptor of ErbB4 (Table 2).

6. Comparative Studies of $\Delta\Delta G_{binding}$ from the Separate Trajectories of NRG-1β Arg31Ala and Asn47Ala Mutations To check the validity of the assumption whether the alanine mutations do not cause large conformational changes for the global structure of NRG-1β/ErbB3 and NRG-1β/ErbB4 complexes, two molecular dynamics simulations for Arg31Ala and Asn47Ala mutants of NRG-1β in the complex with ErbB3 and ErbB4 were performed. The RMSD values of $C_\alpha$ atoms between the average structure of the trajectories of the mutant complexes and the starting model structure are small, fluctuating between 1.9 and 2.1 Å. $\Delta G_{subtotal}$ values recalculated based on the new trajectories of the mutant complexes, as listed in Table 5, are almost identical to the results derived from the modified trajectories of wild-type complexes. The differences between $\Delta G_{subtotal}$ values calculated using two methods are less than 1 kcal·mol$^{-1}$ (Table 5). This indicates that global conformations of NRG-1β/ErbB3 and NRG-1β/ErbB4 do not change dramatically after single alanine mutation.

TABLE 5

Comparison of the components of the binding free energy of the Arg31Ala and Asn47Ala complex with ErbB receptors calculated from the modified trajectory of wild type and from the trajectories collected for the NRG-1β Arg31Ala and Asn47Ala mutants.

| | Arg31Ala modified trajectory of the wild type[a] | | Trajectory of the Arg31Ala mutant[b] | | Asn47Ala modified trajectory of the wild type[a] | | Trajectory of the Asn47Ala mutant[b] | |
|---|---|---|---|---|---|---|---|---|
| | Mean | Std | Mean | Std | Mean | Std | Mean | Std |
| ErbB3 Contribution | | | | | | | | |
| $\Delta E_{ele}$ | −375.84 | 25.66 | −481.47 | 28.15 | −443.90 | 27.79 | −547.58 | 15.65 |
| $\Delta E_{vdw}$ | −141.02 | 7.16 | −143.31 | 7.28 | −140.22 | 6.72 | −151.41 | 5.89 |
| $\Delta E_{gas}$ | −516.86 | 25.50 | −624.78 | 27.24 | −584.12 | 27.45 | −698.99 | 15.56 |
| $\Delta G_{nonpolar}$ | −7.80 | 0.39 | −8.51 | 0.60 | −7.99 | 0.50 | −9.44 | 0.34 |
| $\Delta G_{PB}$ | 488.48 | 25.81 | 596.67 | 28.29 | 550.12 | 26.29 | 646.72 | 15.97 |
| $\Delta G_{sol}$ | 480.68 | 25.65 | 586.16 | 28.12 | 542.13 | 26.11 | 657.27 | 15.93 |
| $\Delta G_{subtotal}$ | −36.18 | 7.30 | −36.62 | 7.55 | −42.01 | 6.86 | −41.71 | 7.82 |
| ErbB4 Contribution | | | | | | | | |
| $\Delta E_{ele}$ | −341.13 | 27.04 | −382.51 | 20.14 | −371.70 | 27.00 | −476.51 | 9.18 |
| $\Delta E_{vdm}$ | −128.92 | 6.64 | −151.00 | 6.14 | −130.88 | 6.78 | −139.35 | 5.93 |
| $\Delta E_{gas}$ | −470.04 | 26.18 | −533.51 | 19.18 | −502.58 | 26.43 | −615.88 | 18.92 |
| $\Delta G_{nonpolar}$ | −7.26 | 0.52 | −8.46 | 1.29 | −7.58 | 0.51 | −8.09 | 0.41 |
| $\Delta G_{PB}$ | 447.59 | 25.20 | 511.86 | 19.34 | 480.25 | 25.32 | 593.59 | 14.90 |

TABLE 5-continued

Comparison of the components of the binding free energy of the Arg31Ala and Asn47Ala complex with ErbB receptors calculated from the modified trajectory of wild type and from the trajectories collected for the NRG-1β Arg31Ala and Asn47Ala mutants.

|  | Arg31Ala modified trajectory of the wild type[a] | | Trajectory of the Arg31Ala mutant[b] | | Asn47Ala modified trajectory of the wild type[a] | | Trajectory of the Asn47Ala mutant[b] | |
|---|---|---|---|---|---|---|---|---|
|  | Mean | Std | Mean | Std | Mean | Std | Mean | Std |
| $\Delta G_{sol}$ | 440.33 | 25.08 | 503.40 | 19.65 | 472.67 | 25.19 | 585.51 | 14.80 |
| $\Delta G_{subtotal}$ | −29.71 | 9.14 | −30.11 | 22.59 | −29.91 | 10.24 | −30.37 | 13.36 |

[a]Calculated for the modified trajectories of the wild type by computational alanine-scanning mutagenesis experiments.
[b]Calculated for the separate trajectories collected for the NRG-1β mutants.

7. Comparative Studies of the Receptor Binding Affinity and Signal Transduction Ability of Neuregulin and its Mutations To study the receptor binding affinity of neuregulin and its mutations, ErbB2&ErbB3 or ErB2&ErB4 co-expressing COST are used. The cells are grown to 80% confluence. In the afternoon, after the cells reach 80% confluence, the media is changed to serum free media. Then, after 24 hours, the cells are harvested for receptor binding affinity assays.

Similarly, to study the signal transduction ability of neuregulin and its mutations, ErbB2&ErbB3 or ErbB2&ErbB4 co-expressing COS7 cells are used. The cells are grown to 80% confluence. In the afternoon, after the cells reach 80% confluence, the media is changed to serum free media. Then after 24 hours, different amounts of neuregulin or neuregulin variants are added into separate wells containing the cells. After 10 minutes, loading buffer is added to lyse the cells. The sample is then harvested and loaded into a separate well of gel for electrophoresis and western blot analysis.

Figure 9:
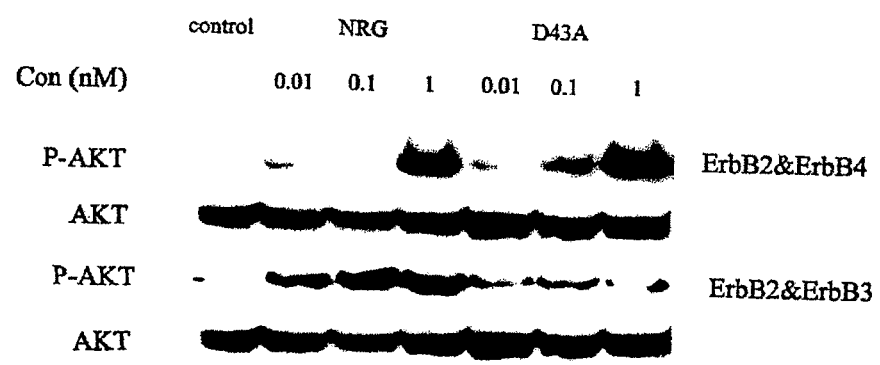
FIG. 9 shows phosphorylation of AKT in ErbB2&ErbB4 and ErbB2&ErbB3 co-expressing COS7 cells after treatment with neuregulin or its mutation (D43A). In the Figure, Con means the concentration of neuregulin, P-AKT means phosphorylation of AKT.
Figure 10:
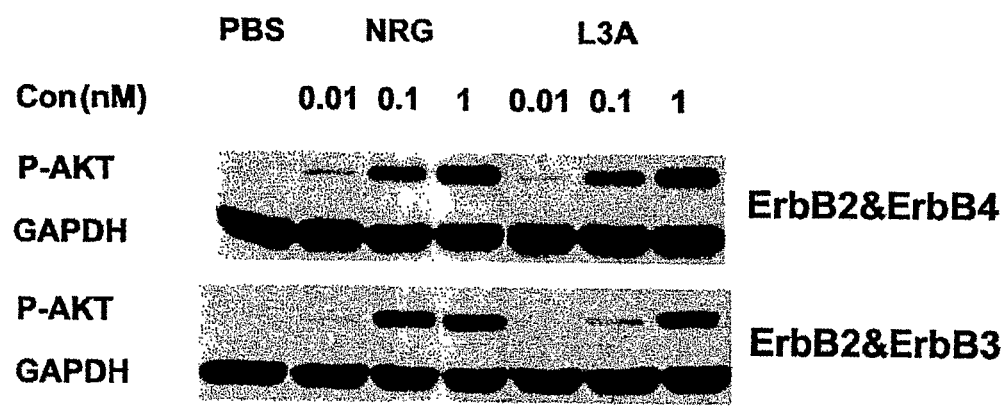
FIG. 10 shows phosphorylation of AKT in ErbB2&ErbB4 and ErbB2&ErbB3 co-expressing COS7 cells after treatment with neuregulin or its mutation (L3A). GAPDH is shown as control of protein amount.

The results for neuregulin (the 177-237 amino acids fragment of neuregulin1 (32) and neuregulin variants L3A and D43A (alanine substitutions for the $3^{rd}$ and $43^{rd}$ amino acids, respectively, of the neuregulin fragment) are shown in Table 6, Table 7, FIG. 9 and FIG. 10. The data in Table 6 and Table 7 show that L3A and D43A have nearly the same receptor binding affinity for ErbB2&ErbB3 co-expressing cells as neuregulin (if the EC50 or KD value is higher, then the receptor binding affinity is lower), while D43A has a much higher (Table 6) and L3A has a much lower (Table 7) receptor binding affinity for ErbB2&ErbB4 co-expressing cells than neuregulin. Similarly, FIGS. 9 and 10 show that L3A and D43A binding induces more AKT phosphorylation than neuregulin in ErbB2&ErbB4 co-expressing cells, but less AKT phosphorylation than neuregulin in ErbB2&ErbB3 co-expressing cells. These results show that L3A and D43A binding can strongly activate AKT signaling pathway in ErbB2&ErbB4 co-expressing cells, but only activate a little in ErbB2&ErbB3 co-expressing cells. These results are significant because cardiac cells primarily express ErbB2&ErbB4, and variants, such as D43A and L3A, can therefore be used to treat cardiovascular diseases while reducing the side effect of neuregulin binding other ErbB2&ErbB3 expressing cells.

TABLE 6

Comparison of the receptor binding affinity of neuregulin and variant D43A on COS7 cells expressing ErbB2/ErbB3 and ErbB2/ErbB4, respectively.

|  | EC50 (nM) | |
|---|---|---|
| Name | COS7 cells (ErbB2&ErbB3 co-expression) | COS7 cells (ErbB2&ErbB4 co-expression) |
| NRG | 112.9 | 132.4 |
| D43A | 149.2 | 40.66 |

EC50 is the concentration of ligands which can compete 50% of bound radiolabeled ligands off the receptor complex.

TABLE 7

Comparison of the receptor binding affinity of neuregulin and variant L3A on COS7 cells expressing ErbB2/ErbB3 and ErbB2/ErbB4, respectively.

|  | EC50 (nM) | |
|---|---|---|
| Name | COS7 cells (ErbB2&ErbB3 co-expression) | COS7 cells (ErbB2&ErbB4 co-expression) |
| NRG | 1407 | 281.6 |
| L3A | 1151 | 1060 |

KD equals ([ligand] × [receptor])/[ligand receptor complex], it reflects the off rate of ligand from receptor.
[ligand] stands for the concentration of ligand.

Figure 11:
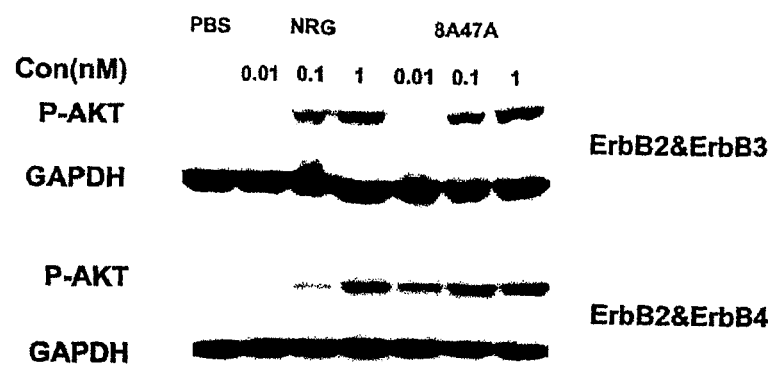
FIG. 11 shows phosphorylation of AKT in ErbB2&ErbB4 and ErbB2&ErbB3 co-expressing COS7 cells after treatment with neuregulin or its double mutant (8A47A). GAPDH is shown as control of protein amount.

Neuregulin double mutant 8A47A (simultaneous alanine substitutions for the $8^{th}$ and $47^{th}$ amino acids of the neuregulin fragment) were constructed. The same method as above was used to study the signal transduction ability of neuregulin and its double mutants. The results for neuregulin (the 177-237 amino acids fragment of neuregulin1β2) and neuregulin double mutant 8A47A (simultaneous alanine substitutions for the $8^{th}$ and $47^{th}$ amino acids of the neuregulin fragment) are shown in FIG. 11. FIG. 11 show that 8A47A binding induces much more AKT phosphorylation than neuregulin in ErbB2&ErbB4 co-expressing cells, but nearly same AKT phosphorylation as neuregulin in ErbB2&ErbB3 co-expressing cells. The result show that 8A47A binding can strongly activate AKT signaling pathway in ErbB2&ErbB4 co-expressing cells, while only normally activate the pathway in ErbB2&ErbB3 co-expressing cells. The result is very important because cardiac cells primarily express ErbB2&ErbB4, so 8A47A can be used to treat cardiovascular diseases while maintaining the side effect of neuregulin binding other ErbB2&ErbB3 expressing cells.

CONCLUSIONS

Homology modeling, molecular dynamics and free energy calculation methods were used to study interactions between NRG-1β and its receptors, ErbB3 and ErbB4. Binding features of NRG-1β to ErbB3 and ErbB4 were addressed using molecular dynamics (MD) simulations. The binding free energies between the ligand and receptor were calculated by the MM-PBSA method. MD simulations revealed that a number of structurally important residues of NRG-1β, such as Leu33, Arg44, Tyr48 and Met 50, are retained for binding to the receptors comparison with corresponding residues of EGF to its receptor. The free energy calculations between the ligand and receptors helped to dissect the origin of binding affinities of NRG-1β to the receptors.

Moreover, the computational alanine-scanning method was used to map the contribution of each residue at the interaction interfaces to the binding affinity, and to validate the constructed models of the ligand-receptor complexes by examining the functions of individual residues at the binding sites. The computational alanine-scanning results identified several important interaction residue pairs, for example in the bindings of NRG-1β to ErbB3 and ErbB4, which shows good agreement with experimental mutagenesis results. This indicates that the current structural models of NRG-1β/ErbB3 and NRG-1β/ErbB4 complexes are reliable and are valuable for selecting desirable mutations on NRG-1β to increase the binding affinity and selectivity to the receptor and discovering new therapeutic agents for the treatment of heart failure, and neuregulin mutations L3A and D43A strongly support this idea.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

---

What is claimed is:

1. A method for preventing, treating, delaying development of viral myocarditis, dilated or congestive cardiomyopathy, cardiac toxicity, or myocardial infarction in an individual, comprising administering to an individual, to which such prevention, treatment or delay is needed or desirable, a pharmaceutical composition comprising an effective amount of a polypeptide variant and a pharmaceutically acceptable excipient, wherein the polypeptide variant is a polypeptide variant of neuregulin-1β comprising the amino acid sequence shown in SEQ ID NO:1, wherein the polypeptide variant comprises one or more different amino acids than that in SEQ ID NO:1, wherein the polypeptide variant has an enhanced binding affinity to ErbB4 compared to the polypeptide of SEQ ID NO:1, and wherein at residue 8 said different amino acid is A;

at residue 16 said different amino acid is A, C, D, E, F, G, H, I, K, L, M, P, Q, R, S, T, V, W, or Y;

at residue 31 said different amino acid is A, C, D, E, F, G, H, I, K, L, M, N, P, Q, S, T, V, W, or Y; or at residue 47 said different amino acid is A, C, D, E, F, G, H, I, K, L, M, P, Q, R, S, T, V, W, or Y.

2. The method of claim 1, wherein the mammal is a human.

3. The method of claim 1, wherein the polypeptide variant consists of SEQ ID NO:1 having one or more different amino acids corresponding to A at residue 8, A, C, D, E, F, G, H, I, K, L, M, P, Q, R, S, T, V, W, or Y at residue 16, A, C, D, E, F, G, H, I, K, L, M, N, P, Q, S, T, V, W, or Y at residue 31, or A, C, D, E, F, G, H, I, K, L, M, P, Q, R, S, T, V, W, or Y at residue 47.

4. The method of claim 1, wherein at residue 16 said different amino acid is A.

5. The method of claim 3, wherein the polypeptide variant consists of one different amino acid at residue 16 and said different amino acid is A.

6. The method of claim 1, wherein at residue 31 said different amino acid is A.

7. The method of claim 3, wherein the polypeptide variant consists of one different amino acid at residue 31 and said different amino acid is A.

8. The method of claim 1, wherein at residue 47 said different amino acid is A.

9. The method of claim 3, wherein the polypeptide variant consists of one different amino acid at residue 47 and said different amino acid is A.

10. The method of claim 1, wherein the polypeptide variant comprises two different amino acids than that in SEQ ID NO:1, wherein the two different amino acids are at residue 47 and at residue 8, and each of said different amino acids is A.

11. The method of claim 3, wherein said polypeptide variant consists of SEQ ID NO:1 having a different amino acid at residue 47 and at residue 8, and each of said different amino acids is A.

12. The method of claim 10, wherein the polypeptide variant induces more Akt phosphorylation in ErbB2/ErbB4 expressing cells compared to the polypeptide of SEQ ID NO:1.

13. The method of claim 11, wherein the polypeptide variant induces more Akt phosphorylation in ErbB2/ErbB4 expressing cells compared to the polypeptide of SEQ ID NO:1.

14. The method of claim 1, wherein the polypeptide variant has a decreased or similar binding affinity to an ErbB3 compared to the polypeptide of SEQ ID NO:1.

15. The method of claim 1, wherein the polypeptide variant comprises 1, 2, 3, or 4 different amino acids than that in SEQ ID NO:1.

* * * * *

SEQUENCE LISTING

```
<160> NUMBER OF SEQ ID NOS: 9

<210> SEQ ID NO 1
<211> LENGTH: 61
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 2
<211> LENGTH: 183
<212> TYPE: DNA
<213> ORGANISM: Homo sapiens

<400> SEQUENCE: 2
agccatcttg taaaatgtgc ggagaaggag aaaactttct gtgtgaatgg aggggagtgc      60
ttcatggtga aagacctttc aaacccctcg agatacttgt gcaagtgccc aaatgagttt     120
actggtgatc gctgccaaaa ctacgtaatg gccagcttct acaaggcgga ggagctgtac     180
cag                                                                  183

<210> SEQ ID NO 3
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Wild type mutation

<400> SEQUENCE: 3

Ser His Leu Val Lys Cys Ala Glu Lys Glu Lys Thr Phe Cys Val Asn
1               5                   10                  15
```

Gly Gly Glu Cys Phe Met Val Leu Asp Leu Ser Asn Pro Ser Arg Tyr
            20                  25                  30

Leu Cys Lys Cys Pro Asn Glu Phe Thr Gly Ala Arg Cys Gln Asn Tyr
        35                  40                  45

Val Met Ala Ser Phe Tyr Lys Ala Glu Glu Leu Tyr Gln
    50                  55                  60

<210> SEQ ID NO 4
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Wild type mutation

<400> SEQUENCE: 4

Ser His Ala Val Lys Cys Ala Glu Lys Glu Lys Thr Phe Cys Val Asn
1               5                   10                  15

Gly Gly Glu Cys Phe Met Val Leu Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 5
<211> LENGTH: 510
<212> TYPE: PRT
<213> ORGANISM: Homo sapiens

<400> SEQUENCE: 5

Glu Lys Lys Val Cys Gln Gly Thr Ser Asn Lys Leu Thr Gln Leu Gly
1               5                   10                  15

Thr Phe Glu Asp His Phe Leu Ser Leu Gln Arg Met Phe Asn Asn Cys
            20                  25                  30

Glu Val Val Leu Gly Asn Leu Glu Ile Thr Tyr Val Gln Arg Asn Tyr
        35                  40                  45

Asp Leu Ser Phe Leu Lys Thr Ile Gln Glu Val Ala Gly Tyr Val Leu
    50                  55                  60

Ile Ala Leu Asn Thr Val Glu Arg Ile Pro Leu Glu Asn Leu Gln Ile
65                  70                  75                  80

Ile Arg Gly Asn Met Tyr Tyr Glu Asn Ser Tyr Ala Leu Ala Val Leu
                85                  90                  95

Ser Asn Tyr Asp Ala Asn Lys Thr Gly Leu Lys Glu Leu Pro Met Arg
            100                 105                 110

Asn Leu Gln Glu Ile Leu His Gly Ala Val Arg Phe Ser Asn Asn Pro
        115                 120                 125

Ala Leu Cys Asn Val Glu Ser Ile Gln Trp Arg Asp Ile Val Ser Ser
    130                 135                 140

Asp Phe Leu Ser Asn Met Ser Met Asp Phe Gln Asn His Leu Gly Ser
145                 150                 155                 160

Cys Gln Lys Cys Asp Pro Ser Cys Pro Asn Gly Ser Cys Trp Gly Ala
                165                 170                 175

Gly Glu Glu Asn Cys Gln Lys Leu Thr Lys Ile Ile Cys Ala Gln Gln
            180                 185                 190

Cys Ser Gly Arg Cys Arg Gly Lys Ser Pro Ser Asp Cys Cys His Asn

```
              195                 200                 205
Gln Cys Ala Ala Gly Cys Thr Gly Pro Arg Glu Ser Asp Cys Leu Val
210                 215                 220

Cys Arg Lys Phe Arg Asp Glu Ala Thr Cys Lys Asp Thr Cys Pro Pro
225                 230                 235                 240

Leu Met Leu Tyr Asn Pro Thr Thr Tyr Gln Met Asp Val Asn Pro Glu
                245                 250                 255

Gly Lys Tyr Ser Phe Gly Ala Thr Cys Val Lys Lys Cys Pro Arg Asn
                260                 265                 270

Tyr Val Val Thr Asp His Gly Ser Cys Val Arg Ala Cys Gly Ala Asp
                275                 280                 285

Ser Tyr Glu Met Glu Glu Asp Gly Val Arg Lys Cys Lys Lys Cys Glu
290                 295                 300

Gly Pro Cys Arg Lys Val Cys Asn Gly Ile Gly Ile Gly Glu Phe Lys
305                 310                 315                 320

Asp Ser Leu Ser Ile Asn Ala Thr Asn Ile Lys His Phe Lys Asn Cys
                325                 330                 335

Thr Ser Ile Ser Gly Asp Leu His Ile Leu Pro Val Ala Phe Arg Gly
                340                 345                 350

Asp Ser Phe Thr His Thr Pro Pro Leu Asp Pro Gln Glu Leu Asp Ile
                355                 360                 365

Leu Lys Thr Val Lys Glu Ile Thr Gly Phe Leu Leu Ile Gln Ala Trp
370                 375                 380

Pro Glu Asn Arg Thr Asp Leu His Ala Phe Glu Asn Leu Glu Ile Ile
385                 390                 395                 400

Arg Gly Arg Thr Lys Gln His Gly Gln Phe Ser Leu Ala Val Val Ser
                405                 410                 415

Leu Asn Ile Thr Ser Leu Gly Leu Arg Ser Leu Lys Glu Ile Ser Asp
                420                 425                 430

Gly Asp Val Ile Ile Ser Gly Asn Lys Asn Leu Cys Tyr Ala Asn Thr
                435                 440                 445

Ile Asn Trp Lys Lys Leu Phe Gly Thr Ser Gly Gln Lys Thr Lys Ile
450                 455                 460

Ile Ser Asn Arg Gly Glu Asn Ser Cys Lys Ala Thr Gly Gln Val Cys
465                 470                 475                 480

His Ala Leu Cys Ser Pro Glu Gly Cys Trp Gly Pro Glu Pro Arg Asp
                485                 490                 495

Cys Val Ser Cys Arg Asn Val Ser Arg Gly Arg Glu Cys Val
                500                 505                 510

<210> SEQ ID NO 6
<211> LENGTH: 505
<212> TYPE: PRT
<213> ORGANISM: Homo sapiens

<400> SEQUENCE: 6

Ala Val Cys Pro Gly Thr Leu Asn Gly Leu Ser Val Thr Gly Asp Ala
1               5                   10                  15

Glu Asn Gln Tyr Gln Thr Leu Tyr Lys Leu Tyr Glu Arg Cys Glu Val
                20                  25                  30

Val Met Gly Asn Leu Glu Ile Val Leu Thr Gly His Asn Ala Asp Leu
                35                  40                  45

Ser Phe Leu Gln Trp Val Arg Glu Val Thr Gly Tyr Val Leu Val Ala
50                  55                  60
```

```
Met Asn Glu Phe Ser Thr Leu Pro Leu Pro Asn Leu Arg Val Val Arg
 65                  70                  75                  80

Gly Thr Gln Val Tyr Asp Gly Lys Phe Ala Ile Phe Val Met Leu Asn
                 85                  90                  95

Tyr Asn Thr Asn Ser Ser His Ala Leu Arg Gln Leu Arg Leu Thr Gln
            100                 105                 110

Leu Thr Glu Ile Leu Ser Gly Val Tyr Ile Glu Lys Asn Asp Lys
        115                 120                 125

Leu Cys His Met Asp Thr Ile Asp Trp Arg Asp Ile Val Arg Asp Arg
    130                 135                 140

Asp Ala Glu Ile Val Lys Asp Asn Gly Arg Ser Cys Pro Pro Cys
145                 150                 155                 160

His Glu Val Cys Lys Gly Arg Cys Trp Gly Pro Gly Ser Glu Asp Cys
                165                 170                 175

Gln Thr Leu Thr Lys Thr Ile Cys Ala Pro Gln Cys Asn Gly His Cys
            180                 185                 190

Phe Gly Pro Asn Pro Asn Gln Cys Cys His Asp Glu Cys Ala Gly Gly
        195                 200                 205

Cys Ser Gly Pro Gln Asp Thr Asp Cys Phe Ala Cys Arg His Phe Asn
210                 215                 220

Asp Ser Gly Ala Cys Val Pro Arg Cys Pro Gln Pro Leu Val Tyr Asn
225                 230                 235                 240

Lys Leu Thr Phe Gln Leu Glu Pro Asn Pro His Thr Lys Tyr Gln Tyr
                245                 250                 255

Gly Gly Val Cys Val Ala Ser Cys Pro His Asn Phe Val Asp Gln
            260                 265                 270

Thr Ser Cys Val Arg Ala Cys Pro Pro Asp Lys Met Glu Val Asp Lys
        275                 280                 285

Asn Gly Leu Lys Met Cys Glu Pro Cys Gly Gly Leu Cys Pro Lys Ala
290                 295                 300

Cys Glu Gly Thr Gly Ser Gly Ser Arg Phe Gln Thr Val Asp Ser Ser
305                 310                 315                 320

Asn Ile Asp Gly Phe Val Asn Cys Thr Lys Ile Leu Gly Asn Leu Asp
                325                 330                 335

Phe Leu Ile Thr Gly Leu Asn Gly Asp Pro Trp His Lys Ile Pro Ala
            340                 345                 350

Leu Asp Pro Glu Lys Leu Asn Val Phe Arg Thr Val Arg Glu Ile Thr
        355                 360                 365

Gly Tyr Leu Asn Ile Gln Ser Trp Pro Pro His Met His Asn Phe Ser
    370                 375                 380

Val Phe Ser Asn Leu Thr Thr Ile Gly Gly Arg Ser Leu Tyr Asn Arg
385                 390                 395                 400

Gly Phe Ser Leu Leu Ile Met Lys Asn Leu Asn Val Thr Ser Leu Gly
                405                 410                 415

Phe Arg Ser Leu Lys Glu Ile Ser Ala Gly Arg Ile Tyr Ile Ser Ala
            420                 425                 430

Asn Arg Gln Leu Cys Tyr His His Ser Leu Asn Trp Thr Lys Val Leu
        435                 440                 445

Arg Gly Pro Thr Glu Glu Arg Leu Asp Ile Lys His Asn Arg Pro Arg
    450                 455                 460

Arg Asp Cys Val Ala Glu Gly Lys Val Cys Asp Pro Leu Cys Ser Ser
465                 470                 475                 480

Gly Gly Cys Trp Gly Pro Gly Pro Gly Gln Cys Leu Ser Cys Arg Asn
```

```
                      485                 490                 495
Tyr Ser Arg Gly Gly Val Cys Val Thr
                500                 505

<210> SEQ ID NO 7
<211> LENGTH: 509
<212> TYPE: PRT
<213> ORGANISM: Homo sapiens

<400> SEQUENCE: 7

Ser Gln Ser Val Cys Ala Gly Thr Glu Asn Lys Leu Ser Ser Leu Ser
1               5                   10                  15

Asp Leu Glu Gln Gln Tyr Arg Ala Leu Arg Lys Tyr Tyr Glu Asn Cys
            20                  25                  30

Glu Val Val Met Gly Asn Leu Glu Ile Thr Ser Ile Glu His Asn Arg
        35                  40                  45

Asp Leu Ser Phe Leu Arg Ser Val Arg Glu Val Thr Gly Tyr Val Leu
    50                  55                  60

Val Ala Leu Asn Gln Phe Arg Tyr Leu Pro Leu Glu Asn Leu Arg Ile
65                  70                  75                  80

Ile Arg Gly Thr Lys Leu Tyr Glu Asp Arg Tyr Ala Leu Ala Ile Phe
                85                  90                  95

Leu Asn Tyr Arg Lys Asp Gly Asn Phe Gly Leu Gln Glu Leu Gly Leu
            100                 105                 110

Lys Asn Leu Thr Glu Ile Leu Asn Gly Gly Val Tyr Val Asp Gln Asn
        115                 120                 125

Lys Phe Leu Cys Tyr Ala Asp Thr Ile His Trp Gln Asp Ile Val Arg
    130                 135                 140

Asn Pro Trp Pro Ser Asn Leu Thr Leu Val Ser Thr Asn Gly Ser Ser
145                 150                 155                 160

Gly Cys Gly Arg Cys His Lys Ser Cys Thr Gly Arg Cys Trp Gly Pro
                165                 170                 175

Thr Glu Asn His Cys Gln Thr Leu Thr Arg Thr Val Cys Ala Glu Gln
            180                 185                 190

Cys Asp Gly Arg Cys Tyr Gly Pro Tyr Val Ser Asp Cys Cys His Arg
        195                 200                 205

Glu Cys Ala Gly Gly Cys Ser Gly Pro Lys Asp Thr Asp Cys Phe Ala
    210                 215                 220

Cys Met Asn Phe Asn Asp Ser Gly Ala Cys Val Thr Gln Cys Pro Gln
225                 230                 235                 240

Thr Phe Val Tyr Asn Pro Thr Thr Phe Gln Leu Glu His Asn Phe Asn
                245                 250                 255

Ala Lys Tyr Thr Tyr Gly Ala Phe Cys Val Lys Lys Cys Pro His Asn
            260                 265                 270

Phe Val Val Asp Ser Ser Ser Cys Val Arg Ala Cys Pro Ser Ser Lys
        275                 280                 285

Met Glu Val Glu Glu Asn Gly Ile Lys Met Cys Lys Pro Cys Thr Asp
    290                 295                 300

Ile Cys Pro Lys Ala Cys Asp Gly Ile Gly Thr Gly Ser Leu Met Ser
305                 310                 315                 320

Ala Gln Thr Val Asp Ser Ser Asn Ile Asp Lys Phe Ile Asn Cys Thr
                325                 330                 335

Lys Ile Asn Gly Asn Leu Ile Phe Leu Val Thr Gly Ile His Gly Asp
            340                 345                 350
```

```
Pro Tyr Asn Ala Ile Glu Ala Ile Asp Pro Glu Lys Leu Asn Val Phe
        355                 360                 365

Arg Thr Val Arg Glu Ile Thr Gly Phe Leu Asn Ile Gln Ser Trp Pro
    370                 375                 380

Pro Asn Met Thr Asp Phe Ser Val Phe Ser Asn Leu Val Thr Ile Gly
385                 390                 395                 400

Gly Arg Val Leu Tyr Ser Gly Leu Ser Leu Leu Ile Leu Lys Gln Gln
                405                 410                 415

Gly Ile Thr Ser Leu Gln Phe Gln Ser Leu Lys Glu Ile Ser Ala Gly
            420                 425                 430

Asn Ile Tyr Ile Thr Asp Asn Ser Asn Leu Cys Tyr Tyr His Thr Ile
        435                 440                 445

Asn Trp Thr Thr Leu Phe Ser Thr Ile Asn Gln Arg Ile Val Ile Arg
    450                 455                 460

Asp Asn Arg Lys Ala Glu Asn Cys Thr Ala Glu Gly Met Val Cys Asn
465                 470                 475                 480

His Leu Cys Ser Asp Gly Cys Trp Gly Pro Gly Pro Asp Gln Cys
                485                 490                 495

Leu Ser Cys Arg Arg Phe Ser Arg Gly Arg Ile Cys Ile
            500                 505

<210> SEQ ID NO 8
<211> LENGTH: 52
<212> TYPE: PRT
<213> ORGANISM: Homo sapiens

<400> SEQUENCE: 8

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser
    50

<210> SEQ ID NO 9
<211> LENGTH: 49
<212> TYPE: PRT
<213> ORGANISM: Homo sapiens

<400> SEQUENCE: 9

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp
```